United States Patent
Leyh et al.

(10) Patent No.: US 8,454,591 B2
(45) Date of Patent: Jun. 4, 2013

(54) SUBCUTANEOUS ELECTRIC FIELD DISTRIBUTION SYSTEM AND METHODS

(75) Inventors: Greg Leyh, Brisbane, CA (US); Jerzy Orkiszewski, Palo Alto, CA (US)

(73) Assignee: Cutera, Inc., Brisbane, CA (US)

( * ) Notice: Subject to any disclaimer, the term of this patent is extended or adjusted under 35 U.S.C. 154(b) by 0 days.

(21) Appl. No.: 13/441,782

(22) Filed: Apr. 6, 2012

(65) Prior Publication Data

US 2012/0197249 A1 Aug. 2, 2012

Related U.S. Application Data

(62) Division of application No. 12/144,948, filed on Jun. 24, 2008, now Pat. No. 8,172,835.

(60) Provisional application No. 61/207,877, filed on Jun. 5, 2008.

(51) Int. Cl.
 *A61M 1/00* (2006.01)
(52) U.S. Cl.
 USPC .......................................................... 606/34
(58) Field of Classification Search
 USPC .................... 606/32, 33, 34, 41, 42, 35, 14
 See application file for complete search history.

(56) References Cited

U.S. PATENT DOCUMENTS

| | | | |
|---|---|---|---|
| 3,683,923 A | 8/1972 | Anderson | |
| 4,140,130 A | 2/1979 | Storm, III | |
| 4,200,104 A | 4/1980 | Harris | |
| 4,416,276 A | 11/1983 | Newton et al. | |
| 4,416,277 A | 11/1983 | Newton et al. | |
| 4,527,550 A | 7/1985 | Ruggera et al. | |
| 4,657,015 A | 4/1987 | Irnich | |
| 4,776,350 A | 10/1988 | Grossman et al. | |
| 4,848,335 A | 7/1989 | Manes | |
| 4,959,631 A | 9/1990 | Hasegawa et al. | |
| 5,052,407 A | 10/1991 | Hauser et al. | |
| 5,063,932 A | 11/1991 | Dahl et al. | |
| 5,111,812 A | 5/1992 | Swanson et al. | |
| 5,143,063 A | 9/1992 | Fellner | |
| 5,472,442 A | 12/1995 | Klicek | |
| 5,480,399 A | 1/1996 | Hebborn | |
| 5,496,312 A | 3/1996 | Klicek | |
| 5,599,344 A | 2/1997 | Paterson | |

(Continued)

FOREIGN PATENT DOCUMENTS

CA 1219642 3/1987

OTHER PUBLICATIONS

Final Office Action received for U. S. Appl. No. 12/330,032, mailed on Jun. 21, 2012, 19 pages.

(Continued)

*Primary Examiner* — Laura A Bouchelle
*Assistant Examiner* — Brooke Matney
(74) *Attorney, Agent, or Firm* — Morrison & Foerster LLP

(57) ABSTRACT

Apparatus and methods for dynamically controlling electric field distribution within tissue disposed at various depths beneath the skin at a target region of a patient's body by independently controlling the electric potential of each of a plurality of electrodes in relation to the electric potential of a ground pad. By controlling electric field distribution during a procedure, a target tissue at particular depths beneath the skin can be selectively heated relative to adjacent non-target tissue. At least one of the electrodes and the ground pad may comprise a spiral inductor comprising a substantially planar spiral of electrically conductive material.

20 Claims, 17 Drawing Sheets

U.S. PATENT DOCUMENTS

| | | | |
|---|---|---|---|
| 5,599,346 | A | 2/1997 | Edwards et al. |
| 5,836,942 | A | 11/1998 | Netherly et al. |
| 5,837,001 | A | 11/1998 | Mackey |
| 6,059,778 | A | 5/2000 | Sherman |
| 6,063,075 | A | 5/2000 | Mihori |
| 6,083,221 | A | 7/2000 | Fleenor et al. |
| 6,235,020 | B1 | 5/2001 | Cheng et al. |
| 6,240,323 | B1 | 5/2001 | Calenzo, Sr. et al. |
| 6,258,085 | B1 | 7/2001 | Eggleston |
| 6,379,350 | B1 | 4/2002 | Sharkey et al. |
| 6,413,255 | B1 | 7/2002 | Stern |
| 6,423,057 | B1 | 7/2002 | He et al. |
| 6,488,678 | B2 | 12/2002 | Sherman |
| 6,544,258 | B2 | 4/2003 | Fleenor et al. |
| 6,635,056 | B2 | 10/2003 | Kadhiresan et al. |
| 6,638,275 | B1 | 10/2003 | McGaffigan et al. |
| 6,860,881 | B2 | 3/2005 | Sturm et al. |
| 7,151,964 | B2 | 12/2006 | Desai et al. |
| 7,160,295 | B1 | 1/2007 | Garito et al. |
| 7,169,145 | B2 | 1/2007 | Isaacson et al. |
| 7,250,047 | B2 | 7/2007 | Anderson et al. |
| 7,278,991 | B2 | 10/2007 | Morris et al. |
| 7,706,890 | B2 | 4/2010 | Palti |
| 7,736,357 | B2 | 6/2010 | Lee, Jr. et al. |
| 7,771,419 | B2 | 8/2010 | Carmel et al. |
| 2002/0058938 | A1 | 5/2002 | Cosmescu |
| 2002/0072664 | A1 | 6/2002 | Katzenmaier et al. |
| 2002/0147467 | A1 | 10/2002 | Bernabei |
| 2003/0163185 | A1 | 8/2003 | Carson |
| 2003/0236487 | A1 | 12/2003 | Knowlton |
| 2004/0158240 | A1 | 8/2004 | Avrahami |
| 2005/0080409 | A1 | 4/2005 | Young et al. |
| 2005/0234444 | A1 | 10/2005 | Hooven |
| 2006/0009756 | A1 | 1/2006 | Francischelli et al. |
| 2006/0036300 | A1 | 2/2006 | Kreindel |
| 2006/0074411 | A1 | 4/2006 | Carmel et al. |
| 2006/0079872 | A1 | 4/2006 | Eggleston |
| 2006/0224150 | A1 | 10/2006 | Arts et al. |
| 2006/0235286 | A1 | 10/2006 | Stone et al. |
| 2007/0049914 | A1 | 3/2007 | Eggleston |
| 2007/0055333 | A1 | 3/2007 | Forde et al. |
| 2007/0167942 | A1 | 7/2007 | Rick |
| 2007/0203482 | A1 | 8/2007 | Ein-Gal |
| 2007/0239075 | A1 | 10/2007 | Rosenberg et al. |
| 2007/0244478 | A1 | 10/2007 | Bahney |
| 2007/0282318 | A1 | 12/2007 | Spooner et al. |
| 2008/0312651 | A1 | 12/2008 | Pope et al. |
| 2009/0171341 | A1 | 7/2009 | Pope et al. |
| 2009/0171344 | A1 | 7/2009 | Pontis |
| 2009/0171346 | A1 | 7/2009 | Leyh |
| 2009/0306647 | A1 | 12/2009 | Leyh et al. |
| 2010/0022999 | A1 | 1/2010 | Gollnick et al. |
| 2010/0211061 | A1 | 8/2010 | Leyh |

OTHER PUBLICATIONS

Non Final Office Action received for U.S. Appl. No. 11/966,881, mailed on Aug. 17, 2011, 15 pages.

Non Final Office Action received for U.S. Appl. No. 11/764,094, mailed on May 12, 2011, 14 pages.

Non Final Office Action received for U.S. Appl. No. 11/966,895, mailed on Sep. 2, 2011, 33 pages.

Final Office Action received for U.S. Appl. No. 12/134,119, mailed on Oct. 7, 2011, 13 pages.

Non Final Office Action received for U.S. Appl. No. 12/134,119, mailed on Apr. 29, 2011, 19 pages.

Non Final Office Action received for U.S. Appl. No. 12/144,948, mailed on Jul. 13, 2011, 17 pages.

Notice of Allowance received for U.S. Appl. No. 12/144,948, mailed on Jan. 19, 2012, 14 pages.

Final Office Action received for U.S. Appl. No. 12/330,032, mailed on Dec. 22, 2011, 29 pages.

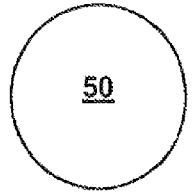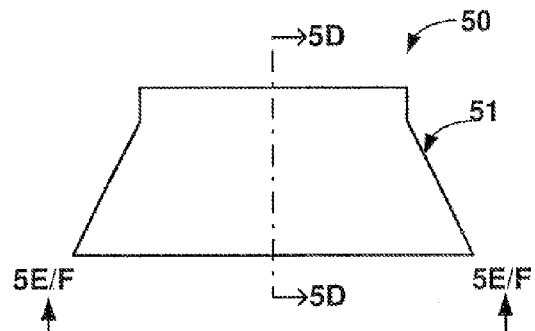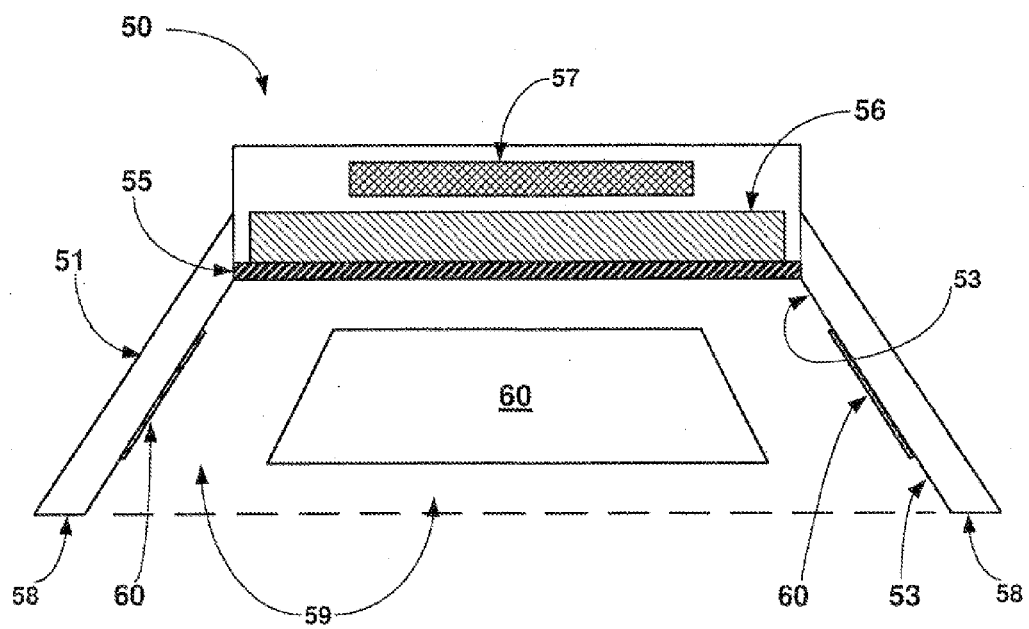

SUBCUTANEOUS ELECTRIC FIELD DISTRIBUTION SYSTEM AND METHODS

CROSS REFERENCE TO RELATED APPLICATIONS

This application is a Divisional of copending U.S. patent application Ser. No. 12/144,948, with a filing date of Jun. 24, 2008, which claims the benefit of U.S. Provisional Application No. 61/207,877, filed Jun. 5, 2008, the disclosure of which is incorporated herein by reference in their entirety.

FIELD OF THE INVENTION

The present invention generally relates to systems and methods for controlling electric field distribution within a patient's tissues.

BACKGROUND OF THE INVENTION

The proportion of children, adolescents, and adults who are overweight or obese is increasing. The number of overweight people has doubled in the last two to three decades, and such increases are found in all age, race, and gender groups.

Cellulite is a common skin condition related to the accumulation of excess subcutaneous fat (adipose tissue) within fibrous septae. Irregularities in the structure of the fibrous septae can create the appearance of cellulite, which is typically seen as an unsightly irregular, dimpled skin surface. Cellulite is often found in abundance in overweight and obese individuals, e.g., on the thighs, hips, and buttocks.

There is a demand for apparatus and procedures that will reduce the overall volume of adipose tissue and/or reshape subcutaneous fat. There is also a demand for treatments that will decrease the appearance of cellulite for cosmetic purposes.

Prior art interventions for decreasing or reshaping adipose tissue include liposuction and lipoplasty, massage, low level laser therapy, and external topical compositions, such as "cosmeceuticals," or a combination of such treatments. Liposuction and lipoplasty are invasive surgical techniques in which subcutaneous fat is excised and/or suctioned from the body. These procedures may be supplemented by the application to the targeted adipose tissue of various forms of energy to emulsify the fat prior to its removal, e.g., by suction.

Although liposuction and lipoplasty can effectively remove subcutaneous fat, the invasive nature of these procedures presents the inherent disadvantages of surgery, including high cost and extended recovery times, as well as the associated risks such as infection, excessive bleeding, and trauma.

Non-invasive interventions for subcutaneous fat reduction, or diminution of the appearance of cellulite, including massage and low-level laser therapy, are significantly less effective than surgical intervention.

Some cosmetic skin treatments effect dermal heating by applying radiofrequency (RF) energy to the skin using surface electrodes. The local heating is intended to tighten the skin by producing thermal injury that changes the ultrastructure of collagen in the dermis, and/or results in a biological response that changes the dermal mechanical properties. The literature has reported some atrophy of sub-dermal fat layers as a complication to skin tightening procedures.

During electrosurgical procedures that target subcutaneous fat, the depth of muscle tissue below the surface of the skin may greatly influence the distribution of electric currents, and therefore the heating distribution within the tissues. Prior art apparatus and methods have not adequately addressed electric current distribution in subcutaneous tissue in relation to variations in the thickness or depth of skeletal muscle tissue underlying a targeted tissue comprising subcutaneous fat.

US Patent Application Publication No. 2006/0036300 (Kreindel) discloses lipolysis apparatus having one or more protruding, terminal electrodes. In methods of Kreindel, a region of tissue may be deformed, and the electrodes may contact both deformed and non-deformed skin.

U.S. Pat. No. 6,488,678 to Sherman discloses apparatus including a catheter having an array of electrodes at the catheter distal end, and adapted to position the electrodes at a biological site. A backplate is positioned proximal to the biological site, such that the biological site is interposed between the backplate and the electrodes. Power provided to the electrodes has a duty cycle with on and off periods. During a first segment of the on period, energy flows between the backplate and an electrode, while during a second segment of the on period, energy flows between the electrodes. The flow of energy can be controlled by adjusting the phase angle of the power.

U.S. Pat. No. 6,635,056 to Kadhiresan et al. discloses a system including a catheter for use in ablation therapy, e.g., of cardiac tissue, in which the system uses controllable differences in amplitude of power signals to establish repetitive bipolar current flow between sets of electrodes, and a backplate to establish unipolar current flow.

U.S. Pat. No. 7,151,964 to Desai discloses a multi-electrode catheter for ablation of endocardiac tissues. The electrodes are adapted for being collapsed for introducing the catheter into the patient's body, and for being fanned out into an array during ablation of tissue, such as endomyocardium. In a preferred embodiment of the '964 patent, a two-phase RF power source is used with an orthogonal electrode catheter array comprising one central electrode and four peripheral electrodes. The central electrode is connected to ground voltage of the power supply; and the peripheral electrodes form two diagonal pairs connected to two individually phased voltages.

U.S. Patent Application Publication No. 2007/0203482 (Ein Gal) discloses a system including at least two target electrodes, at least one return electrode, and at least two RF power sources in electrical communication with the electrodes. Each target electrode defines a separate monopolar energy delivery channel, the at least one return electrode being common to both channels. The target electrodes are operable in a bipolar mode. A waveform manipulator controls and manipulates RF energy waveforms to the target electrodes to selectively provide pure monopolar, pure bipolar and a blend of monopolar and bipolar modes of energy delivery for RF tissue ablation.

It can be seen that there is a need for an effective modality by which subcutaneous fat tissue may be non-invasively reshaped, and/or sculpted for the cosmetic improvement of human skin and/or body shape. There is a further need for a non-invasive procedure for effectively and efficiently decreasing the volume of subcutaneous adipose tissue in a person who may be obese or overweight.

SUMMARY OF THE INVENTION

According to one aspect of the invention, a system for treating a target issue of a patient includes a handpiece configured for contacting skin of the patient, an electrosurgical generator coupled to the handpiece, and a ground pad coupled to the electrosurgical generator. The handpiece includes at least a first electrode and a second electrode, and the system is configured for independently controlling an electric potential of each of the first electrode, the second electrode, and the ground pad, such that the system is adapted for dynamically controlling electric current distribution relative to a depth of the target tissue beneath the skin.

According to another aspect of the invention there is provided a system for treating a patient, the system including a ground pad, an electrosurgical generator coupled to the ground pad, and a handpiece coupled to the electrosurgical generator. The handpiece includes a shell having a treatment chamber therein, a treatment surface within the treatment chamber, and a plurality of electrodes disposed on the treatment surface. The system is configured for independently controlling an electric potential of each of the electrodes relative to a reference potential of the ground pad.

According to yet another aspect of the invention, a method for treating a patient includes providing a handpiece having at least a first electrode and a second electrode; disposing a ground pad against a non-target region of the patient's skin; contacting the handpiece against the patient's skin, such that at least the first electrode and the second electrode contact a target region of the patient's skin; and independently controlling an electric potential of each of the first electrode, the second electrode, and the ground pad. The method further includes applying electrical energy to a target tissue via at least one of the first electrode and the second electrode; and dynamically controlling electric current distribution relative to a depth beneath the skin of the target issue, such that the target tissue is selectively heated. The target tissue is disposed beneath the target region of the patient's skin.

According to still a further aspect of the invention, there is provided a method for selectively heating a target tissue of a patient, wherein the method includes providing a handpiece having a plurality of electrodes, a treatment chamber, and a flange; contacting a ground pad against a non-target region of the patient's skin; contacting the flange against the patient's skin, such that the flange surrounds a target region of the patient's skin; drawing the target tissue into the treatment chamber; and maintaining the ground pad at a reference potential. The method further includes independently controlling an electric potential of each of the electrodes relative to the reference potential; and applying electrical energy to the target tissue via at least one of the electrodes, such that electric current distribution relative to the target tissue is dynamically controlled to provide selective heating of the target tissue. The target tissue comprises subcutaneous fat disposed beneath the target region of the patient's skin.

These and other features, aspects, and advantages of the present invention may be further understood with reference to the drawings, description, and claims which follow.

BRIEF DESCRIPTION OF THE DRAWINGS

FIGS. 5A-B each show a plan view of a handpiece, as seen from above, according to two different embodiments of the invention;

FIG. 5C is a side view of the handpiece of FIG. 5A or 5B;

FIG. 5D is a sectional view of the handpiece of FIGS. 5A-C, as seen along the line 5D-5D of FIG. 5C;

DETAILED DESCRIPTION OF THE INVENTION

Figure 1A:
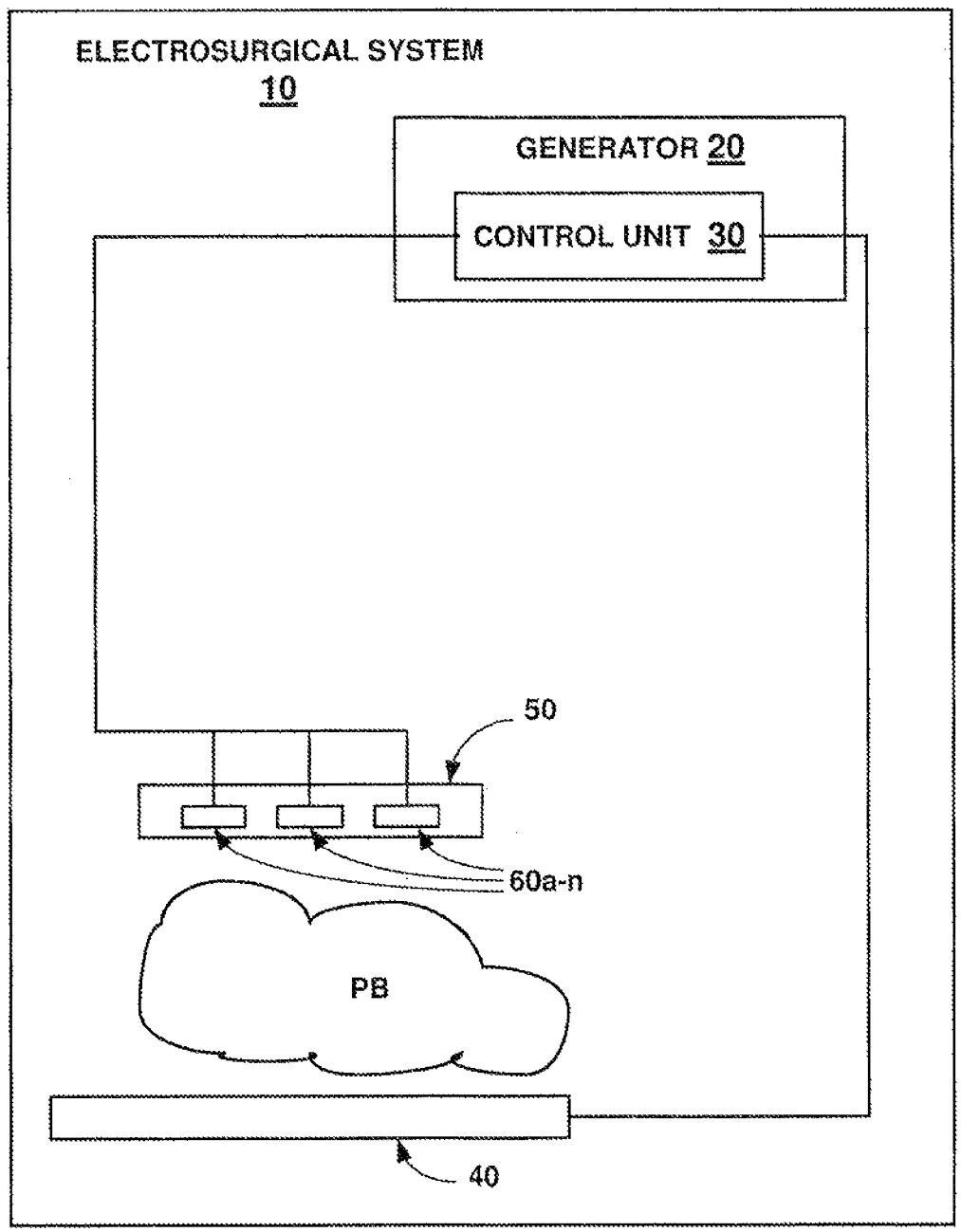
FIG. 1A schematically represents an electrosurgical system for treating a patient, according to an embodiment of the invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides methods and apparatus for treating or selectively heating a target tissue of a patient in a non-invasive procedure. As a non-limiting example, the instant invention may be used to selectively heat, remove, and or sculpt adipose tissue, such as may be present in subcutaneous fat and/or cellulite.

During electrosurgical procedures that target subcutaneous fat, the effective depth of skeletal muscle tissue below the surface of the skin may greatly influence the distribution of electric currents, and therefore the heating distribution within the tissues. The skeletal muscle depth can vary widely from patient to patient, as well as from region to region of a given patient's body. To tailor a procedure for a particular region of a given patient's body and to compensate for wide variations in tissue, the instant invention actively controls the distribution of electric currents, and therefore the distribution of heat, e.g., relative to tissue depth below the skin surface. Such current distribution control can be achieved by adjusting or controlling the potential difference between at least two (active) electrodes disposed on a target region of the skin surface; and, at the same time, by controlling the potential difference between at least one of the electrodes relative to a ground pad.

Apparatus of the invention may include a handpiece having a plurality of electrodes configured for contacting the patient's skin, wherein an electric potential of at least two of the electrodes may be independently controlled during a procedure to dynamically control electric current distribution within a patient's tissue relative to a depth of a target tissue disposed beneath, and adjacent to, the patient's skin.

Apparatus and systems of the instant invention may include a handpiece configured for contacting a treatment surface of the handpiece against a target region of the skin surface, wherein a plurality of electrodes may be disposed on the treatment surface, such that at least two of the electrodes contact the target region of skin during treatment of the patient. At least one of the electrodes may be a substantially planar spiral inductor, and each electrode may be affixed to and aligned with the treatment surface. Systems and apparatus of the instant invention may further include a ground pad. The ground pad may comprise a substantially planar spiral inductor configured for contacting the patient's skin. Each spiral inductor (of the electrodes and/or ground pad) may be formed from a substantially planar spiral of electrically conductive material.

During a procedure according to an embodiment of the instant invention, the ground pad may be disposed in contact with a non-target region of the skin surface of the patient. The non-target region of the skin may be remote from the target region of the skin, such that at least one layer of subcutaneous fat, at least one layer of skeletal muscle, and/or at least one bone of the patient may be disposed between the handpiece and the ground pad.

FIG. 1A schematically represents an electrosurgical system for treating a patient, according to an embodiment of the invention. System 10 may include an electrosurgical generator 20, a ground pad 40, and a handpiece 50. Ground pad 40 and handpiece 50 may be coupled to electrosurgical generator 20. Ground pad 40 may function as a return electrode. During a procedure involving system 10, ground pad 40 may be located on the skin of the patient at a location remote from the surgical site/handpiece 50. System 10 may further include a control unit 30. In an embodiment, control unit 30 may be integral with generator 20. In another embodiment, control unit 30 may comprise a separate device.

Handpiece 50 may include a plurality of electrodes 60a-n. Each of electrodes 60a-n may be in electrical communication with control unit 30. System 10 may be configured for independently controlling, e.g., via control unit 30, an electric potential of each of electrodes 60a-n. For example, during a procedure system 10 may be configured for independently controlling or dynamically adjusting an electric potential of each of electrodes 60a-n relative to a reference potential of ground pad 40. In an embodiment, system 10 may be configured for independently controlling a potential difference between: i) a first electrode 60a and ground pad 40, ii) a second electrode 60b and ground pad 40, and iii) first electrode 60a and second electrode 60b. In an embodiment, system 10 may be configured for maintaining ground pad 40 at a reference potential. Such reference potential may correspond to ground (earth) potential. In an embodiment, system 10 may be configured for providing a first AC voltage to first electrode 60a and for providing a second AC voltage to second electrode 60b. System 10 may be configured for dynamically controlling, e.g., via control unit 30, a phase difference between the first and second AC voltages, such that a potential difference between first and second electrodes 60a-b can be controlled during a procedure. Dynamic control of the potential difference between first and second electrodes 60a-b may include adjusting a phase difference between the first and second AC voltages, i.e., the phase difference between the first and second AC voltages may determine the potential difference between first and second electrodes 60a-b.

What has been described herein with reference to controlling electric potential of first and second electrodes 60a-b may similarly be applicable to each of electrodes 60a-n. The electric potential of each of electrodes 60a-n may be dynamically controlled during a procedure, e.g., to selectively heat a target tissue to an appropriate temperature or temperature range, relative to adjacent non-target tissue.

Figure 8A:
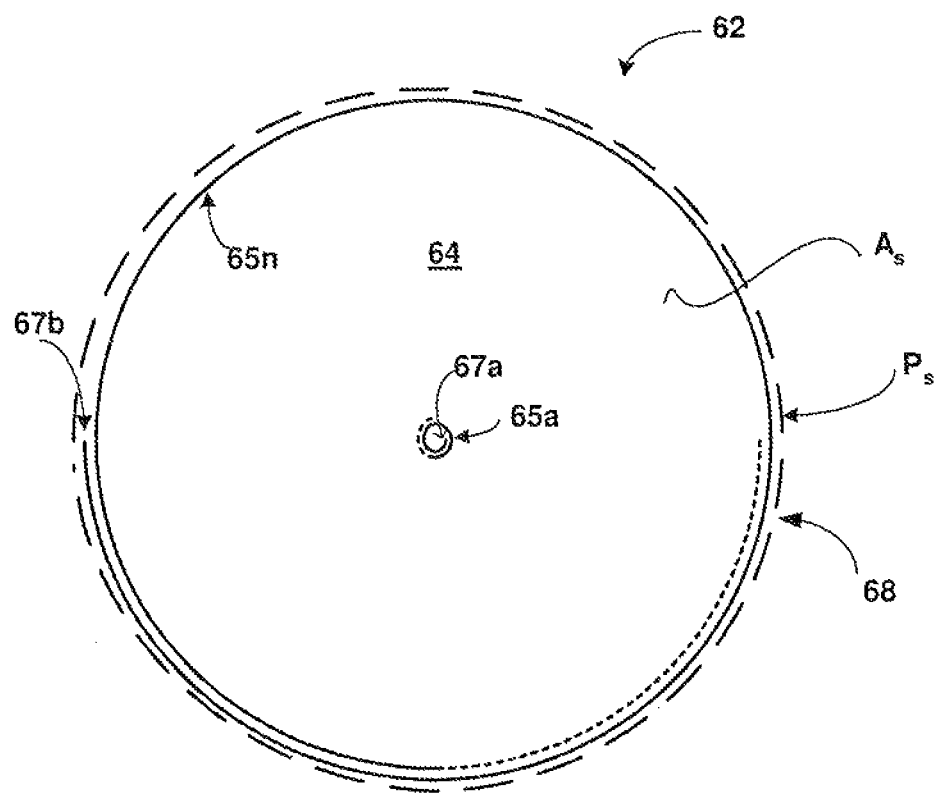
FIG. 8A schematically represents a spiral inductor, as seen in plan view, according to an embodiment of the invention.
Figure 8B:
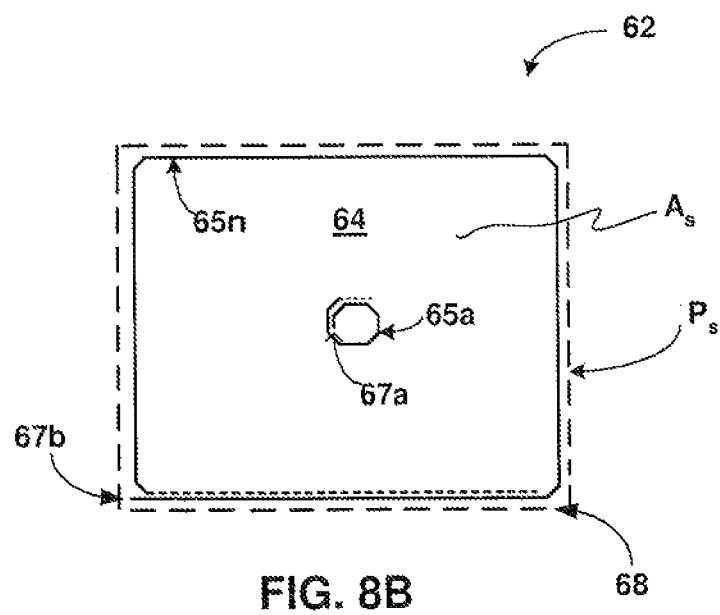
FIG. 8B schematically represents a spiral inductor, as seen in plan view, according to another embodiment of the invention.

In an embodiment, ground pad 40 may comprise a spiral inductor 62 (see, e.g., FIGS. 8A-B). In an embodiment, one or more of electrodes 60a-n may similarly comprise a spiral inductor. In an embodiment, handpiece 50 may have a substantially planar treatment surface 53, i.e., treatment surface 53 may occupy a single plane (see, e.g., FIGS. 6A-B). In other embodiments, handpiece 50 may have a treatment surface 53 that occupies a plurality of different planes (see, e.g., FIGS. 5D-E).

During use of system 10, e.g., for performing an electrosurgical procedure, a patient's body, PB, or a portion thereof, may be juxtaposed between ground pad 40 and handpiece 50. System 10 may be adapted for treating a patient for the reduction of cellulite, for sculpting the external surface of the patient's body, and for decreasing an amount of subcutaneous fat of the patient, or a combination thereof, or similar procedures. System 10 may be used for improving the appearance of the external portion of a patient's body, for reduction in body weight of the patient, or for a combination thereof, or for similar purposes. Typically, during a procedure involving system 10, at least one layer of subcutaneous fat, at least one layer of skeletal muscle, and/or at least one bone of the patient may be disposed between handpiece 50 and ground pad 40 (see, e.g., FIG. 12B).

Figure 1B:
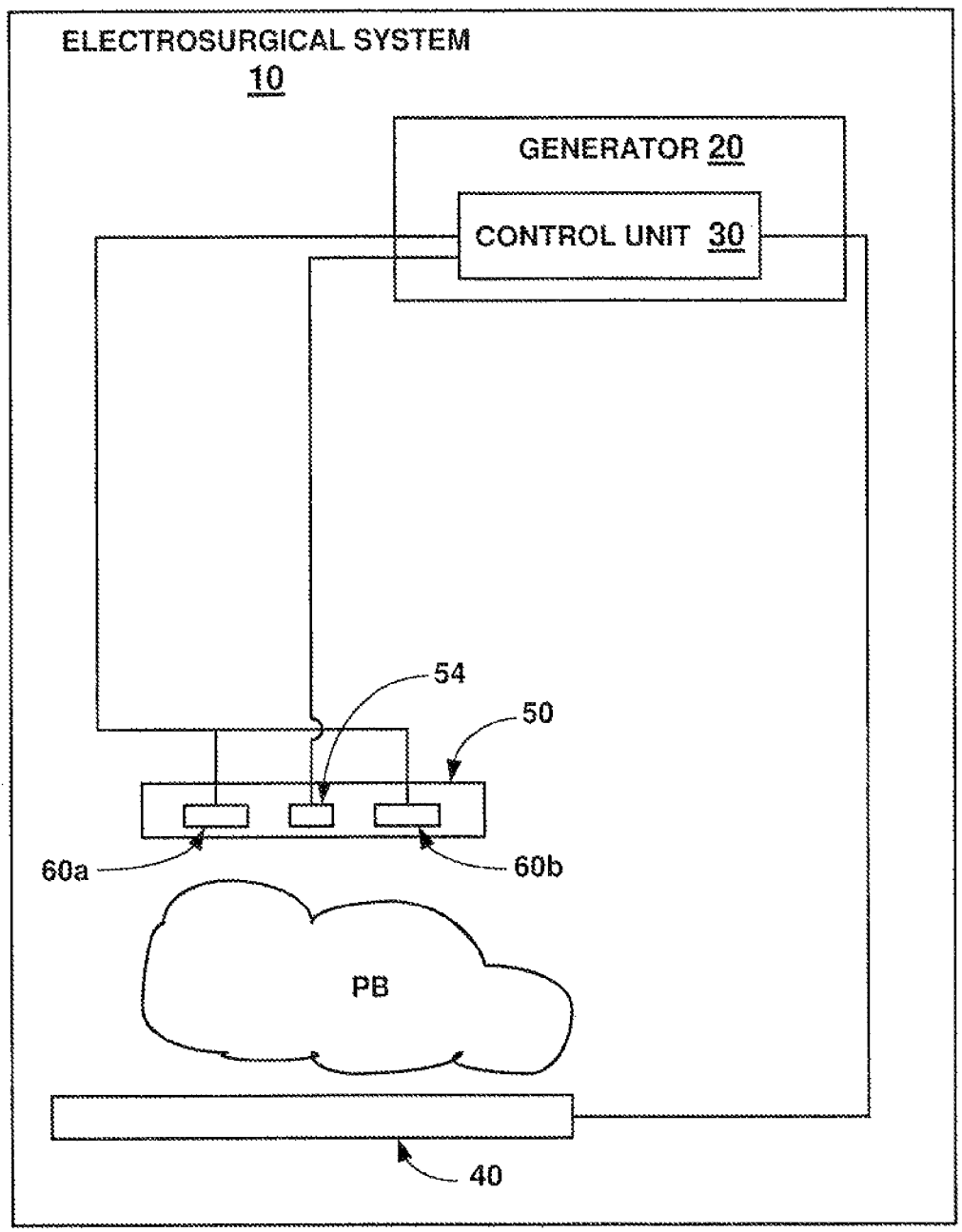
FIG. 1B schematically represents an electrosurgical system for treating a patient, according to another embodiment of the invention.

FIG. 1B schematically represents an electrosurgical system for treating a patient, according to another embodiment of the invention. System 10 of FIG. 1B may have components, elements, and features generally as described with reference to FIG. 1A (supra), including handpiece 50, generator 20, ground pad 40, and control unit 30. Handpiece 50 and ground pad 40 may be coupled to control unit 30. Control unit 30 may be integral with generator 20. The invention is not limited to any particular configuration for system 10.

Handpiece 50 of FIG. 1B may include at least two electrodes, including first electrode 60a and second electrode 60b. In an embodiment, the at least two electrodes may be disposed at least substantially opposite each other, e.g., first electrode 60a may be disposed opposite second electrode 60h (see, e.g., FIGS. 5E and 6A).

With further reference to FIG. 1B, handpiece 50 may further include at least one temperature sensor 54. Temperature sensor 54 may be in communication with control unit 30. Temperature sensor 54 may be configured for sensing temperature values of a portion of a target region of skin. In an embodiment, system 10 may be configured for sensing a temperature value of a target tissue, e.g., via extrapolation of a sensed skin temperature. Temperature sensor 54 may provide sensed temperature values to control unit 30. Control unit 30 may be configured for independently controlling the electric potential of each of first and second electrodes 60a-b, e.g., in response to the sensed temperature values. Control unit 30 may be further configured for independently controlling the electric potential of ground pad 40; for example, system 10 may be configured for controlling the electric potential of ground pad 40 independently of the control of the electric potential of first and second electrodes 60a-b. In an embodiment, handpiece 50 may include a plurality of temperature sensors 54 (see, e.g., FIG. 3A).

Figure 2A:
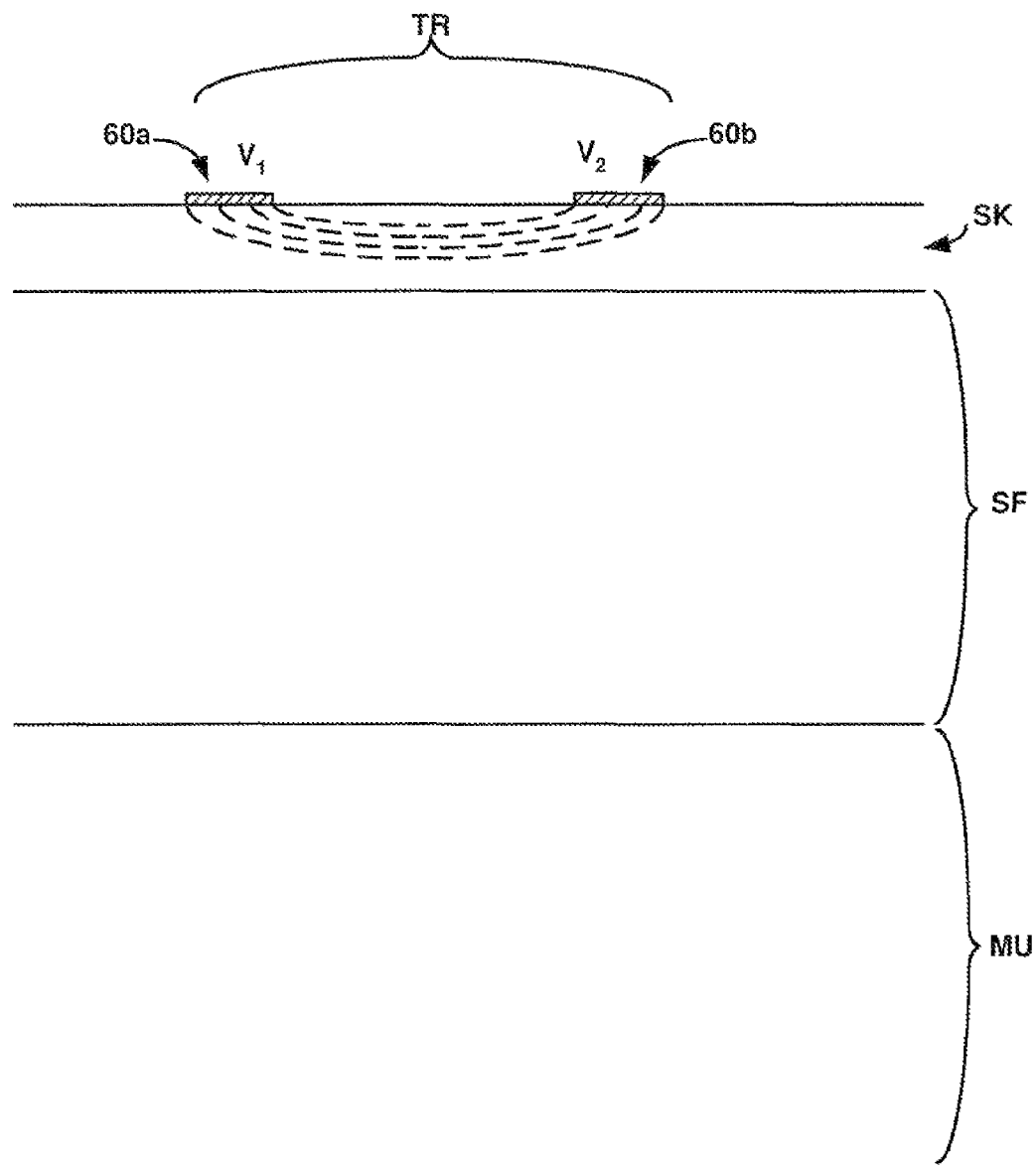
FIG. 2A schematically represents electric current distribution between a first electrode and a second electrode in contact with the skin of a patient in a bipolar mode of operation.

FIG. 2A schematically represents electric current distribution (broken lines) between a first electrode 60a and a second electrode 60b, both of which may be disposed on or within a single handpiece 50 (see, e.g., FIGS. 1A-B). (Handpiece components other than first and second electrodes 60a, 60b are omitted from FIG. 2A for the sake of clarity.) Both of first and second electrodes 60a, 60b may be in contact with a target region, TR, of skin of a patient, in a bipolar mode of operation. First and second electrodes 60a, 60b are shown schematically in relation to a simplified representation of tissue layers of the patient's body, PB, including the skin, SK, subcutaneous fat, SF, and skeletal muscle. MU. (The term "skeletal muscle" is used herein to distinguish the muscle adjacent to the subcutaneous fat from other, fundamentally different forms of muscle found in the human body, namely "cardiac muscle" of the heart and "smooth muscle" of organs such as the stomach. That is to say, the term "skeletal muscle" as used herein excludes both smooth muscle and cardiac muscle.)

Figure 2B:
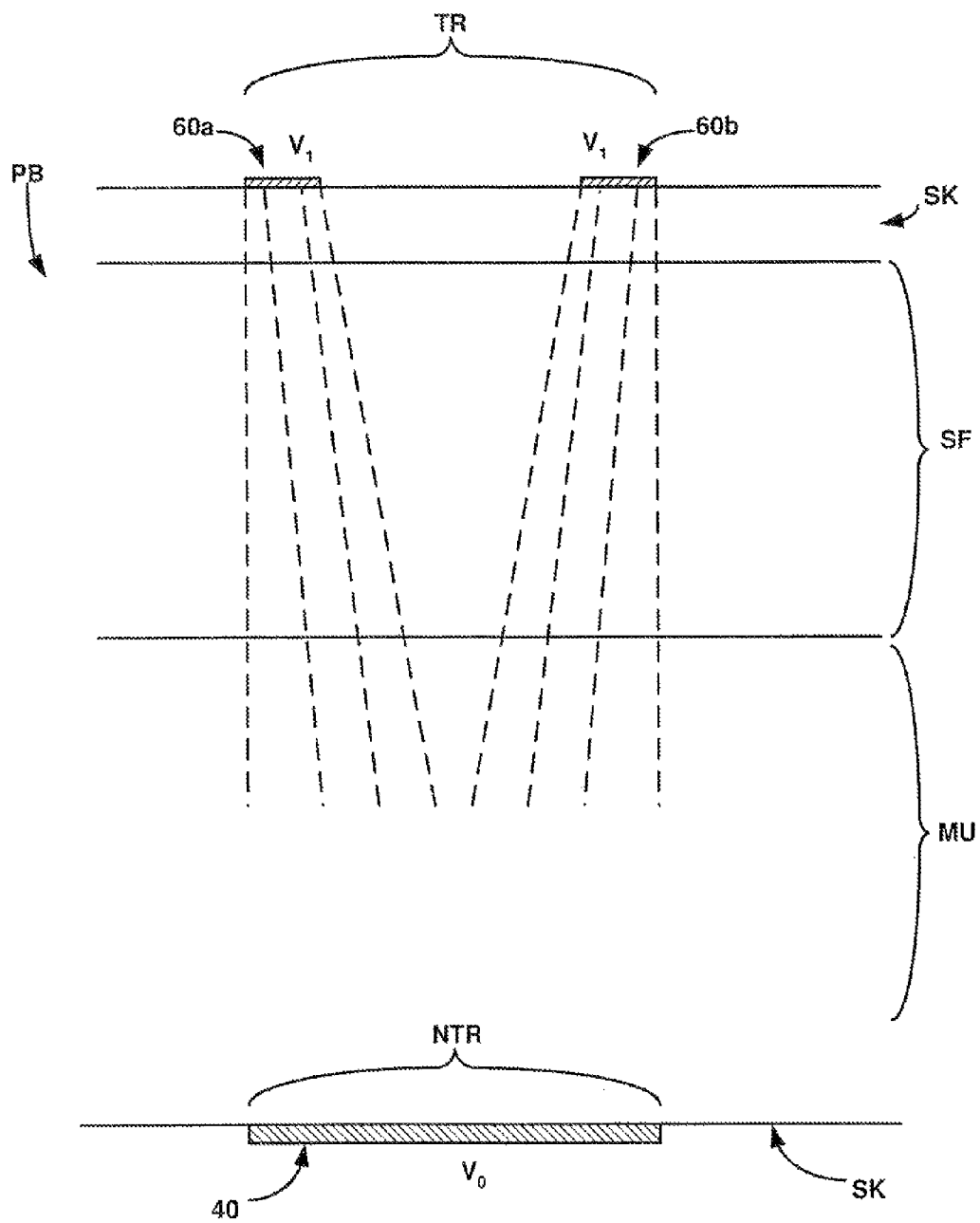
FIG. 2B schematically represents electric current distribution between a ground pad and first and second electrodes, with the first and second electrodes in contact with the skin of a patient, in a monopolar mode of operation.
Figure 2C:
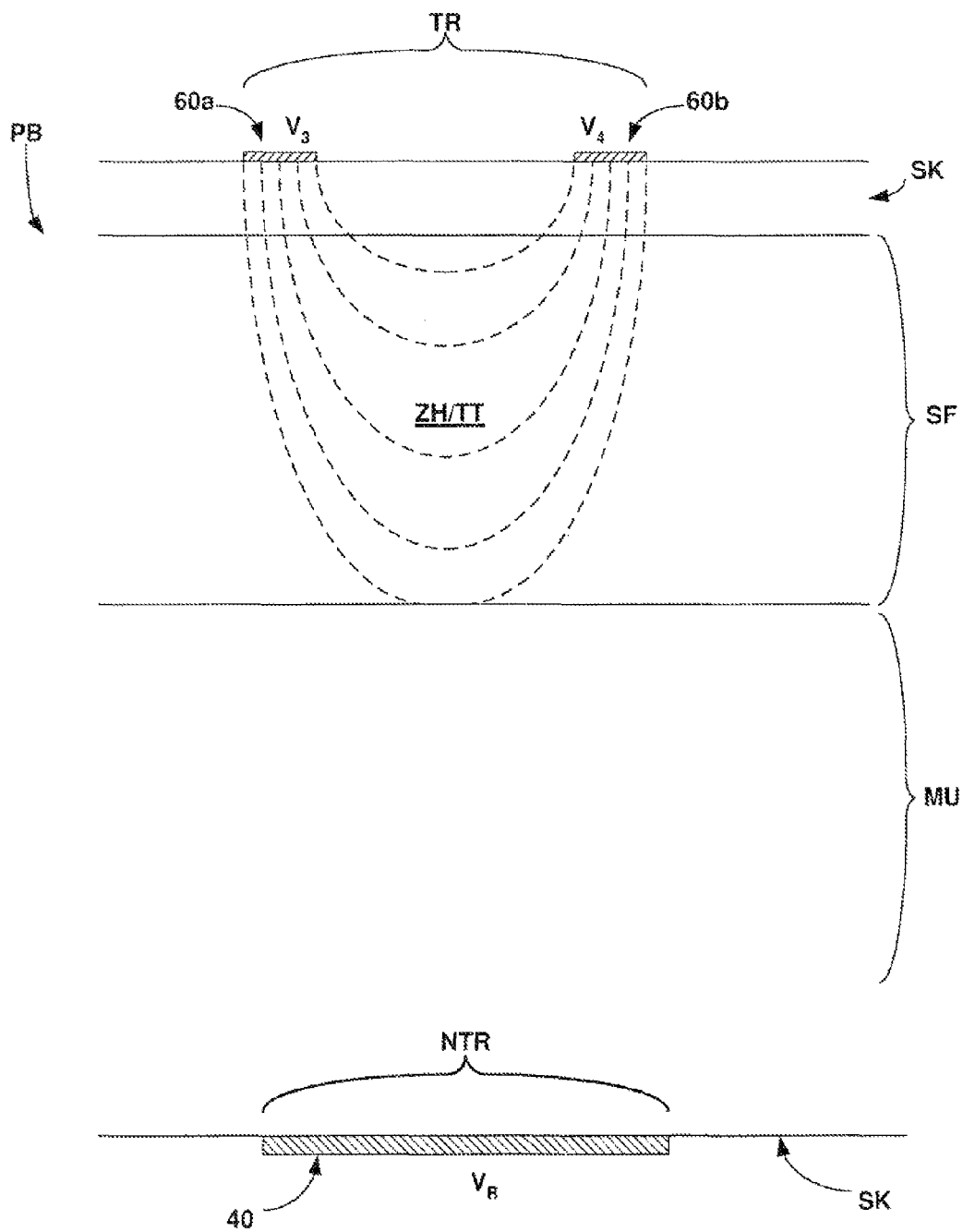
FIG. 2C schematically represents electric current distribution between a first electrode, a second electrode, and a ground pad, with the first and second electrodes in contact with a target region of skin of a patient, according to an aspect of the invention.

First and second electrodes 60a, 60b may be coupled to an electrosurgical generator or power supply (not shown in FIGS. 2A-C). First electrode 60a may be controlled at, or adjusted to, a first electric potential $V_1$ and second electrode 60b may be controlled at, or adjusted to, a second electric potential $V_2$, such that a potential difference exists between first and second electrodes 60a, 60b. In this configuration, electric current tends to flow substantially horizontally (or transversely) between first and second electrodes 60a, 60b. The type of electric current distribution within the tissue as shown in FIG. 2A may result in only shallow heating in the region of the skin; while a deeper target tissue in the subcutaneous fat layer may receive little or no heating from first and second electrodes 60a-b. In FIG. 2A, a ground pad (not shown) may be absent or disconnected from the power supply or generator.

FIG. 2B schematically represents electric current distribution (broken lines) between a ground pad and first and second electrodes, with the first and second electrodes in contact with a target region, TR, of skin of a patient, in a monopolar mode of operation. In FIG. 2B, first and second electrodes 60a, 60b as well as ground pad 40 are shown in relation to the skin, subcutaneous fat, and skeletal muscle layers. Ground pad 40 may be maintained at ground potential, $V_0$. Each of first and second electrodes 60a, 60b may be controlled or maintained at an electric potential $V_1$. In this configuration, there is no potential difference between first and second electrodes 60a, 60, and accordingly electric current tends to flow substantially vertically from first and second electrodes 60a, 60b to ground pad 40, resulting in deeper and more diffuse heating in the skeletal muscle layer (beneath the subcutaneous fat), while the subcutaneous fat may again receive little heating via first and second electrodes 60a-b.

FIG. 2C schematically represents electric current distribution (broken lines) relative to a first electrode, a second electrode, and a ground pad, according to an embodiment of the invention. In FIG. 2C, first and second electrodes 60a, 60b are shown in contact with a target region, TR, of skin, SK, of a patient. A layer of subcutaneous fat, SF, and a skeletal muscle layer, MU, are shown in relation to the skin. In an embodiment, ground pad 40 may be maintained at a reference potential, $V_R$. In an embodiment, the reference potential may comprise ground (earth) potential, e.g., $V_R$ may equal $V_0$. In another embodiment, the ground pad 40 may be controlled or maintained at a reference potential other than ground potential. The electric potential of each of first and second electrodes 60a, 60b, as well as that of ground pad 40, may be independently controlled or adjusted via control unit 30 (see, e.g., FIGS. 1A-B, 3A). For example, an electric potential of first and second electrodes 60a, 60b may be controlled at electric potentials $V_3$ and $V_4$, respectively, wherein $V_3$ and $V_4$ are different, such that a potential difference exists between first and second electrodes 60a, 60h. At least one of $V_3$ and $V_4$ may be different from $V_R$, such that a potential difference exists between at least one of first and second electrodes 60a, 60b with respect to ground pad 40. In an embodiment, each of $V_3$, $V_4$, and $V_R$ may represent a different electric potential, such that a potential difference exists between each of: i) first electrode 60a and second electrode 60b, ii) first electrode 60a and ground pad 40, and iii) second electrode 60b and ground pad 40.

Figure 12A:
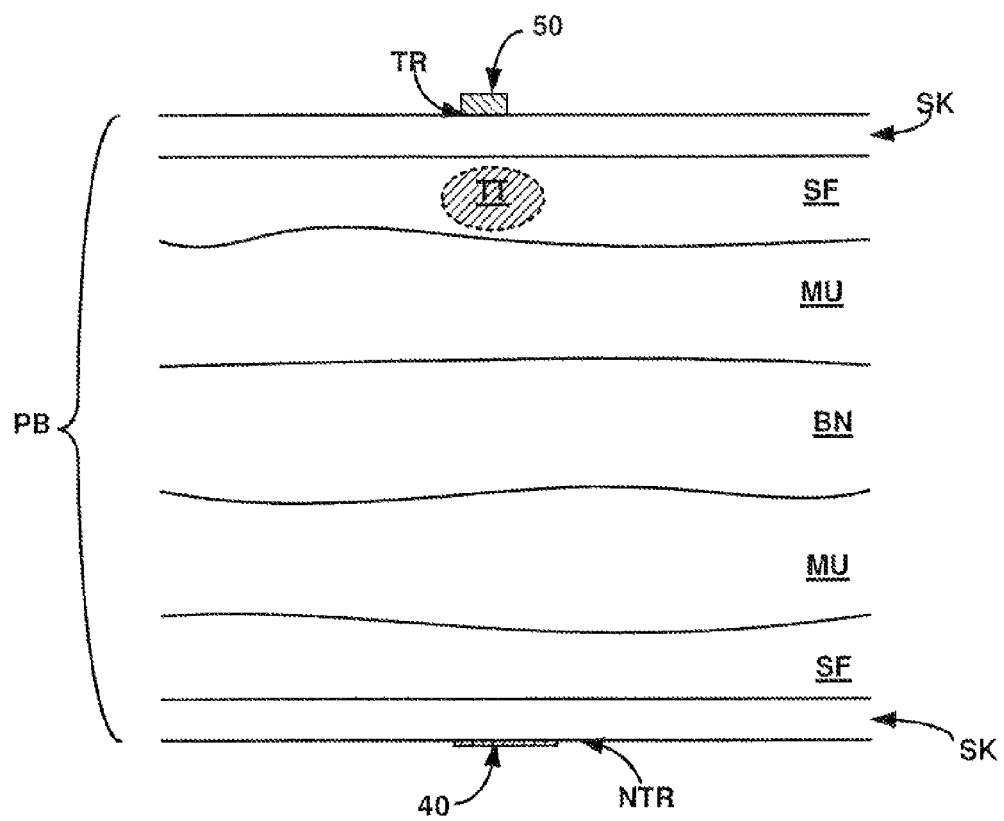
FIG. 12A schematically represents a portion of a patient's body disposed in relation to a handpiece and a ground pad, according to another embodiment of the invention.

During a procedure according to the instant invention, handpiece 50 (not shown in FIGS. 2A-C) and ground pad 40 may be disposed or configured in relation to the patient's body such that at least one bone of the patient (not shown), as well as at least one layer of subcutaneous fat and at least one layer of skeletal muscle may be disposed between handpiece 50 and ground pad 40 (see, e.g., FIG. 12A). In this regard, it is well known in the art that skeletal muscle is disposed beneath subcutaneous fat on the torso and the upper and lower limbs of the human body, and that skeletal muscle is attached to bones.

In the configuration of FIG. 2C, electric current distribution can be dynamically controlled, relative to a depth beneath the skin of the target tissue, TT, by controlling the values of $V_3$, $V_4$, and $V_R$. By dynamically controlling the electric current distribution at different, defined depths beneath the skin, a target tissue at particular depths can be selectively heated. For example, subcutaneous fat, SF, can be selectively heated in relation to the skeletal muscle layer, MU, and the adjacent target region of the skin. The skeletal muscle layer may comprise, as non-limiting examples, the external oblique muscle of the abdomen, the pectoralis major muscle of the thorax, the gluteus maximus of the buttock, the deltoid muscle of the shoulder, the trapezius muscle between the back and neck, the biceps brachii or the triceps brachii muscles of the arm, the latissimus dorsi muscle of the back, or the rectus femoris, biceps femoris, vastus lateralis or vastus medialis muscles of the thigh. Each of the skeletal muscles of the human body described herein is well known in the art (see, e.g., *Atlas of Human Anatomy*, Second Edition (1999), by Frank H. Netter, M.D. (Arthur F. Dailey II, Ph.D., Consulting Editor), Novartis, East Hanover, N.J., the contents of which are incorporated by reference herein).

A schematic representation of an exemplary zone of selective heating, ZH, disposed between the skin and muscle layer is shown in FIG. 2C. It is to be understood, however, that the invention is not limited to a particular electric current distribution or zone of selective heating at any particular depth beneath the skin. Rather, the electric current distribution within the tissue, and hence the zone of selective heating, can be dynamically controlled during a procedure by controlling the values of electric potential, $V_3$, $V_4$, and $V_R$. In other embodiments, electric current distribution within the patient's tissue may be controlled according to the same principles using apparatus having more than two electrodes (see, e.g., FIGS. 1A, 3A, 5E, and 6A).

Figure 3A:
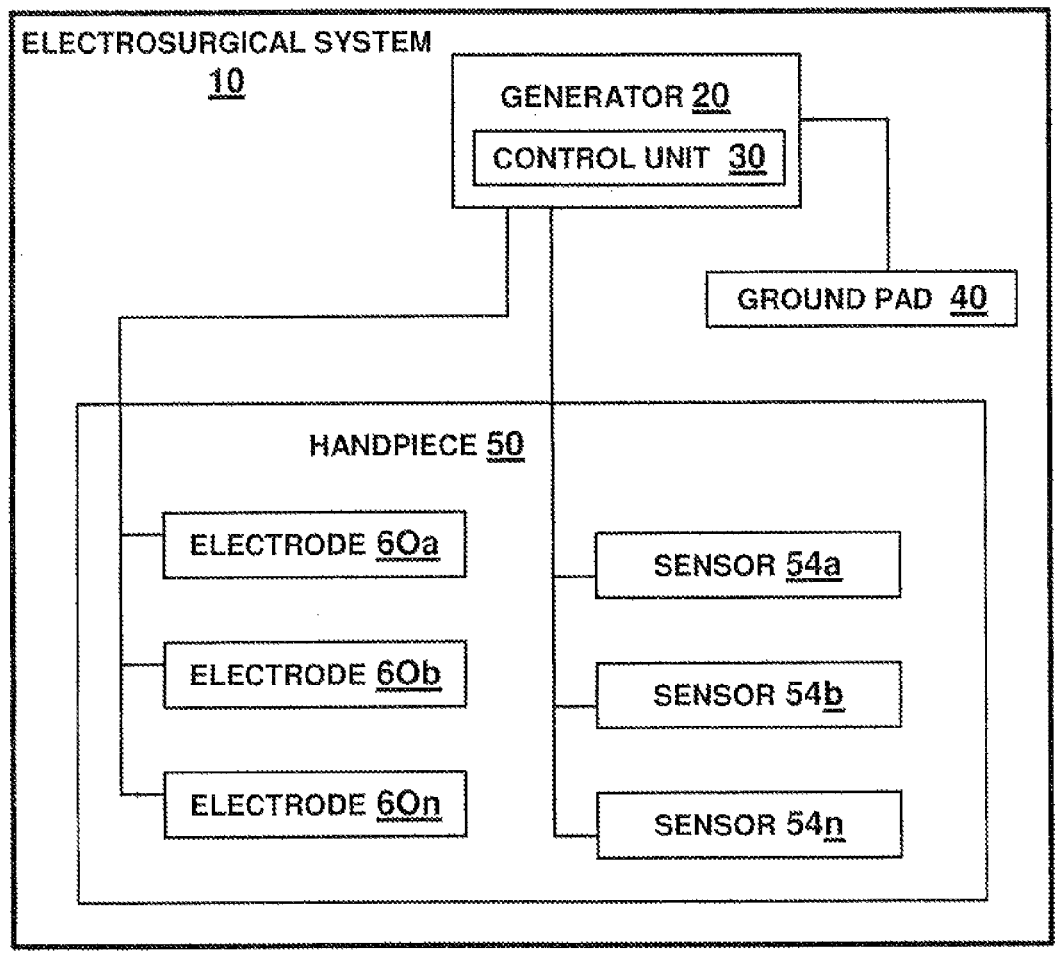
FIG. 3A is a block diagram schematically representing an electrosurgical system including a control unit in communication with a handpiece having a plurality of electrodes and a plurality of temperature sensors, according to an embodiment of the invention.

FIG. 3A is a block diagram schematically representing an electrosurgical system, according to an embodiment of the invention. System 10 may include a handpiece 50, a generator 20, a ground pad 40, and a control unit 30. Handpiece 50 and ground pad 40 may be coupled to control unit 20. Control unit 30 may be integral with generator 20. The invention is not limited to any particular configuration for system 10.

With further reference to FIG. 3A, handpiece 50 may include a plurality of electrodes 60*a-n*. Each of electrodes 60*a-n* may be configured for contacting the skin of a patient. For example, handpiece 50 may be disposed in relation to a patient's body such that each of electrodes 60*a-n* contacts a target region of skin adjacent to a target tissue, such as subcutaneous fat disposed between the target region of skin and a skeletal muscle layer.

Handpiece 50 may further include a plurality of temperature sensors 54*a-n*. Each of temperature sensors 54*a-n* may be configured for contacting the skin of the patient. In an embodiment, temperature sensors 54*a-n* may be disposed within a treatment chamber (not shown in FIG. 3A) of handpiece 50. In an embodiment (not shown), temperature sensors 54*a-n* may be disposed at the periphery, corners, and/or sides of handpiece 50. Each of temperature sensors 54*a-n* may be configured for sensing temperature values of a portion of the target region of skin, wherein the target region of skin may be disposed adjacent to the target tissue. In an embodiment, the target tissue may comprise subcutaneous adipose tissue disposed beneath the target region of skin of the patient (see, e.g., FIG. 2C). Each of temperature sensors 54*a-n* may be in communication with control unit 30 for providing thereto sensed temperature values. Each of electrodes 60*a-n* may be in communication with control unit 30. Generator 20 may include an RF power source (not-shown) in communication with control unit 30. Control unit 30 may be configured for independently controlling an electric potential of each of electrodes 60*a-n* relative to an electric potential of ground pad 40. The electric potential of electrodes 60*a-n* and of ground pad 40 may be dynamically controlled during a procedure, substantially as described hereinabove (e.g., with reference to FIGS. 1A and 2C). In an embodiment, such control of electric potential of electrodes 60*a-n* may be performed in response to temperature values sensed by at least one of temperature sensors 54*a-n*. Control unit 30 may include an analog to digital converter in communication with a CPU, microprocessor, or microcontroller (not shown), and the like; however, the invention is not to be limited to a control unit 30 having particular components, circuitry, or configurations.

Although FIG. 3A shows three temperature sensors 54*a-n*, other numbers of sensors are also within the scope of the invention. Similarly, although FIG. 3A shows three electrodes 60*a-n*, other numbers of electrodes are also within the scope of the invention. As a non-limiting example, handpiece 50 may include from two to ten or more electrodes 60*a-n*, usually from two to eight electrodes 60*a-n*, and often from two to six electrodes 60*a-n*.

Figure 3B:
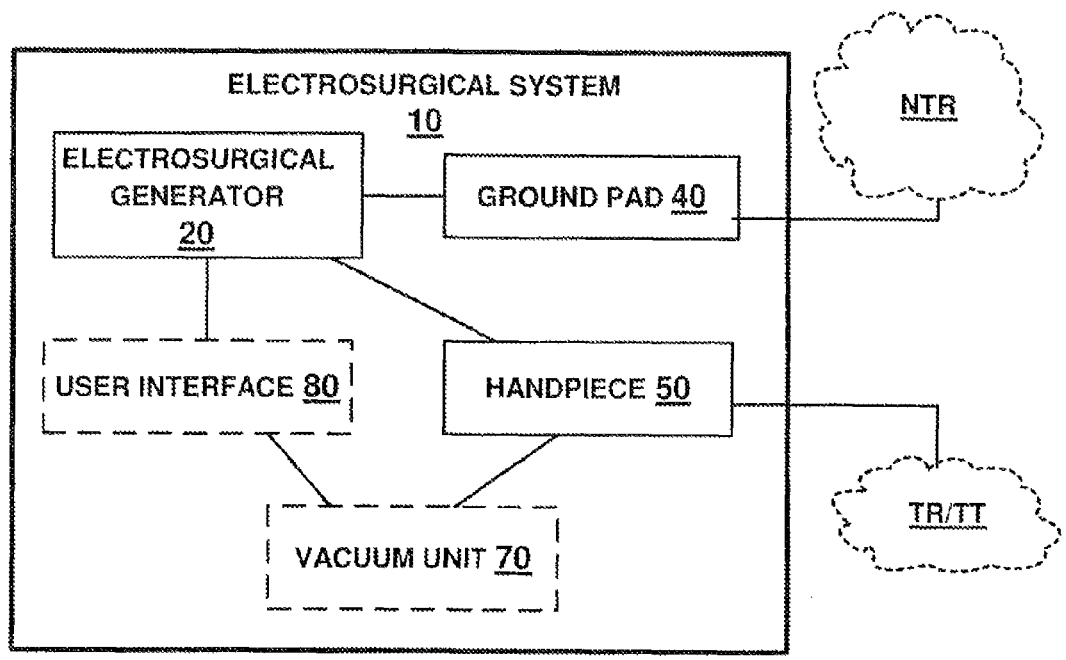
FIG. 3B is a block diagram schematically representing an electrosurgical system including a vacuum unit in communication with a handpiece, according to another aspect of the invention.

FIG. 3B is a block diagram schematically representing an electrosurgical system; according to an embodiment of the invention. System 10 may include a handpiece 50 coupled to an electrosurgical generator 20. Handpiece 50 may be configured for contacting a target region of the skin, SK, located above or adjacent to a target tissue, TT, of the patient. Handpiece 50 may include various elements and characteristics as described hereinabove (e.g., with reference to FIGS. 1A and 3A). In an embodiment, system 10 may further optionally include a vacuum unit 70. Vacuum unit 70 may be in fluid communication with handpiece 50. In an embodiment, handpiece 50 may be configured for drawing a target tissue, such as a volume of subcutaneous fat, within a treatment chamber of handpiece 50 (see, e.g., FIG. 5D).

With further reference to FIG. 3B, system 10 may further include a ground pad 40, which may be configured for contacting the skin of the patient. System 10 may be configured for contacting ground pad 40 against a non-target region, NTR, of the skin during a procedure, wherein the non-target region of the patient's skin may be disposed at a location remote from the target region of the patient's skin. For example, during a procedure at least one layer of subcutaneous fat, at least one layer of skeletal muscle, and/or at least one bone of the patient may typically be disposed between the handpiece at the target region of the skin and the ground pad at the non-target region of the skin. As another example, the handpiece and the target region of the skin may be disposed at an anterior position on the patient's body, while the ground pad and the non-target region of the skin may be disposed at a posterior position on the patient's body.

In an embodiment, system 10 may further include a user interface 80. User interface 80 may be coupled to, or in signal communication with, electrosurgical generator 20, for inputting thereto parameters related to a particular procedure. Such parameters may include threshold temperature values for the target region of skin or target tissue, value(s) of a reference potential for ground pad 40, and the like. User interface 80 may also be coupled to, or in signal communication with, vacuum unit 70, for qualitatively and/or quantitatively controlling the application of suction, via vacuum unit 70, to handpiece 50 (see, e.g., FIG. 10B).

Figure 4:
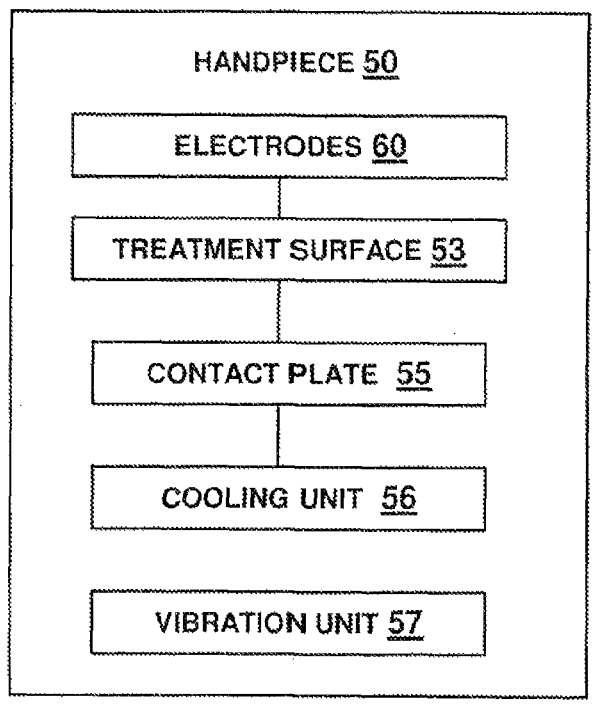
FIG. 4 is a block diagram schematically representing a handpiece having a cooling unit and a vibration unit, according to another embodiment of the invention.

FIG. 4 is a block diagram schematically representing a handpiece, according to another embodiment of the invention. Handpiece 50 may include a plurality of electrodes 60*a-n*, a treatment surface 53, and a contact plate 55. Electrodes 60*a-n* may be disposed on treatment surface 53. Contact plate 55 may be at least substantially planar. Contact plate 55 may be contiguous with treatment surface 53. In an embodiment, handpiece 50 may further include a cooling unit 56. Cooling unit 56 may be disposed against or adjacent to contact plate 55. In an embodiment, cooling unit 56 may be disposed at least substantially parallel to contact plate 55.

Contact plate 55 may be configured to function in concert with cooling unit 56 to cool a target region of the patient's skin during a procedure. In an embodiment, handpiece 50 may still further include a vibration unit 57 configured for vibrating handpiece 50 during a procedure.

FIG. 5A is a plan view of a handpiece, as seen from above, according to an embodiment of the invention. In the embodiment of FIG. 5A, handpiece 50 may have a substantially square or rectangular shape or outline. FIG. 5B is a plan view of a handpiece, as seen from above, according to another embodiment of the invention. In the embodiment of FIG. 5B, handpiece 50 may have a substantially circular or round shape or outline. Naturally, other shapes or outlines for handpiece 50 are also within the scope of the invention.

Figure 5E:
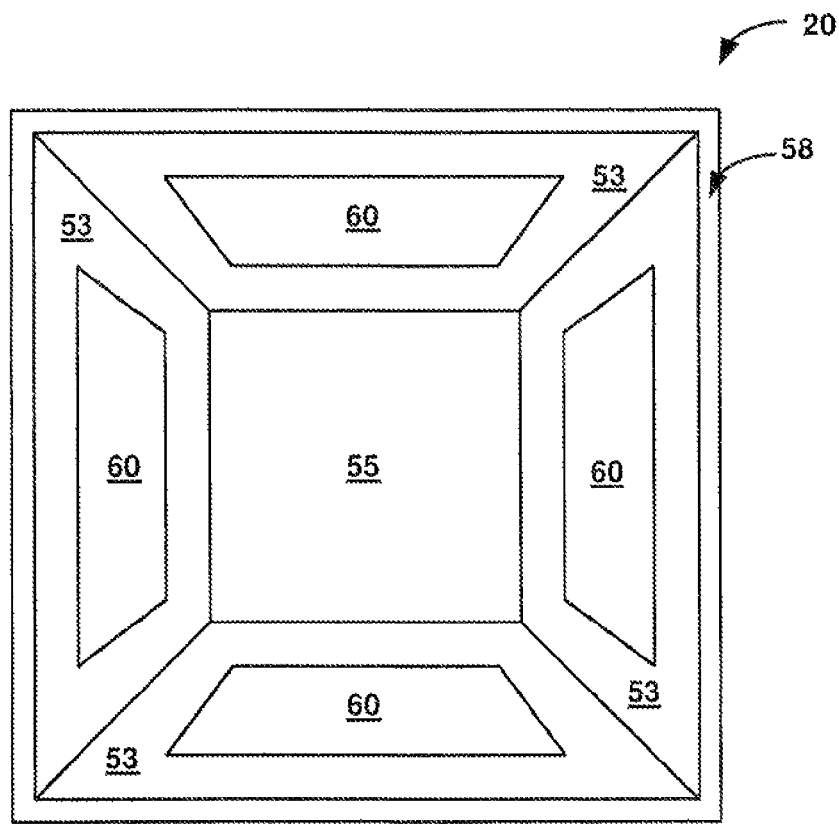
FIG. 5E shows a plan view of the underside of the handpiece of FIG. 5A, as seen along the line 5E/F-5E/F of FIG. 5C.
Figure 5F:
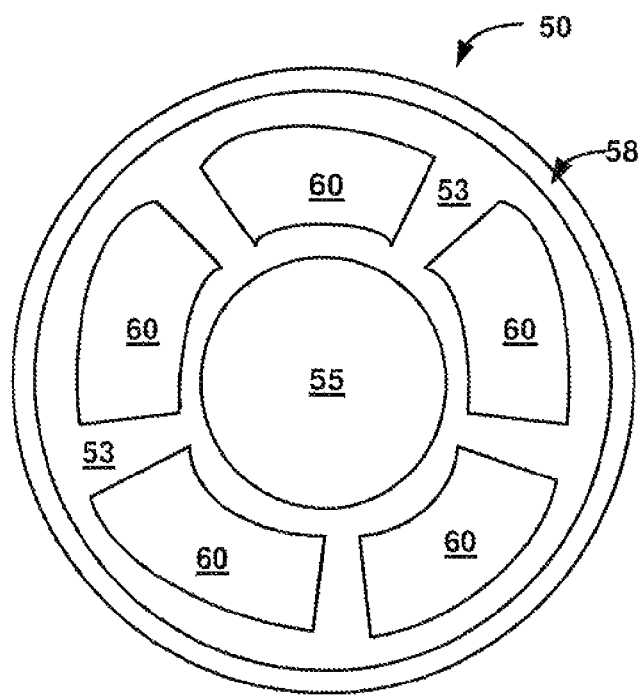
FIG. 5F shows a plan view of the underside of the handpiece of FIG. 5B, as seen along the line 5E/F-5E/F of FIG. 5C.

FIG. 5C is a side view of the handpiece of FIG. 5A or 5B. Handpiece 50 may include a shell 51. Further detail of handpiece 50 is shown in FIGS. 5D-F (infra). FIG. 5D is an enlarged sectional view of the handpiece of FIGS. 5A-C, as seen along the line 5D-5D of FIG. 5C. Handpiece 50 may include shell 51, a flange 58, a treatment surface 53, and a contact plate 55. Handpiece 50 may further include a plurality of electrodes 60. Each electrode 60 may be coupled to control-unit 30 (see, e.g., FIGS. 1A-B), and an electric potential of each electrode 60 may be independently controlled relative to a ground pad potential during a procedure to dynamically control electric current distribution within or adjacent to a target tissue (e.g., subcutaneous adipose tissue) of the patient, substantially as described hereinabove (e.g., with reference to FIGS. 1A and 2C).

In an embodiment, each electrode 60 may be affixed to and aligned with at least a portion of treatment surface 53. Flange 58 may define a distal rim of handpiece 50, and electrodes 60 may be disposed proximal to flange 58. For example, electrodes 60 may be recessed within shell 51/treatment chamber 59. Treatment surface 53 may comprise an electrically insulating or dielectric material. In an embodiment, handpiece 50 may further include a plurality of temperature sensors 54a-n (see, e.g., FIG. 3A). One or more portions of treatment surface 53, and at least one of electrodes 60, may be at least substantially planar. Treatment surface 53 and contact plate 55 may jointly define treatment chamber 59. In an embodiment, handpiece 50 may be configured for receiving at least a portion of a target tissue within treatment chamber 59 during a procedure (see, e.g., FIG. 10B).

In an embodiment, handpiece 50 may further include a cooling unit 56. Cooling unit 56 may be configured for cooling contact plate 55. Contact plate 55 may be at least substantially planar. Contact plate 55 may be contiguous with treatment surface 53. Cooling unit 56 may be disposed against or adjacent to contact plate 55. In an embodiment, cooling unit 56 may be disposed at least substantially parallel to contact plate 55. Contact plate 55 may be configured for cooling a portion of the patient's skin during a procedure. In an embodiment, cooling unit 56 may comprise a thermoelectric cooler (not shown). The cold side of such a thermoelectric cooler (TEC) may be disposed against, or adjacent to, contact plate 55. The hot side of the TEC may be cooled via fluid (e.g., water) flow (not shown). Cooling unit 56 may be configured for cooling contact plate 55 to a temperature down to zero (0°), typically to a temperature in the range of zero (0°) to about 30° C., usually to a temperature in the range of about 10° to 25° C., and often to a temperature in the range of about 16° to 22° C.

In an embodiment, handpiece 50 may still further include a vibration unit 57. As a non-limiting example, vibration unit 57 may comprise an eccentric rotor, which may be of the type shown and described in commonly-owned U.S. application Ser. No. 11/851,335, SYSTEM AND METHOD FOR DERMATOLOGICAL TREATMENT USING ULTRASOUND, filed Sep. 6, 2007. During a procedure, vibration unit 57 may be driven or activated to vibrate at least one of handpiece 50 and target tissue disposed within treatment chamber 59.

FIG. 5E shows a plan view of the underside of handpiece 50 of FIG. 5A, as seen along the line 5E/F-5E/F of FIG. 5C. In the embodiment of FIG. 5E, handpiece 50 may have a substantially square or rectangular shape or outline. FIG. 5E shows flange 58, contact plate 55, and a plurality of electrodes 60 disposed on treatment surface 53. As shown, electrodes 60 may be disposed at least substantially opposite each other on treatment surface 53. Flange 58, contact plate 55, and treatment surface 53 may jointly define treatment chamber 59 (see, e.g., FIGS. 5D and 10A). In the embodiment of FIG. 5E, treatment surface 53 may occupy at least two different planes. At least two of electrodes 60 may be disposed in at least two different planes within treatment chamber 59. In an embodiment, each plane, or each substantially planar portion of treatment surface 53, may have a separate electrode 60 disposed thereon. Electrodes 60 may be configured to accommodate various geometries of treatment surface 53. Each electrode 60 may have a substantially elongate or rectangular shape.

In an embodiment, at least one of electrodes 60 may comprise a spiral inductor 62 (see, e.g., FIGS. 8A-B). In some embodiments, each of electrodes 60 may comprise a spiral inductor 62. Each spiral inductor may comprise a spiral 64 of an electrically conductive metal (see, e.g., FIGS. 7 and 8A-9B). An active electrode comprising a spiral inductor was disclosed in commonly assigned, co-pending U.S. patent application Ser. No. 11/966,895, entitled "High Conductivity Inductively Equalized Electrodes and Methods," the disclosure of which is incorporated by reference herein in its entirety.

In an embodiment of the instant invention, each spiral inductor may have a substantially trapezoidal shape, e.g., comprising a quadrilateral outline having two parallel sides and two non-parallel sides. A spiral electrode having such a quadrilateral outline may also have rounded corners (not shown). In the embodiment of FIG. 5E, treatment chamber 59 may have a substantially frusto-pyramidal (truncated pyramid) shape. A handpiece having a substantially frusto-pyramidal, frusto-conicl (truncated cone), or dome shaped treatment chamber is disclosed in commonly assigned, co-pending U.S. patent application Ser. No. 12/134,119, entitled "Dynamically Controllable Multi-electrode Apparatus & Methods," filed on even date herewith, the disclosure of which is incorporated by reference herein in its entirety.

FIG. 5F shows a plan view of the handpiece of FIG. 5B, as seen along the line 5E/F-5E/F of FIG. 5C. In the embodiment of FIG. 5F, handpiece 50 may have a substantially round or circular shape or outline. FIG. 5A shows flange 58, contact plate 55, and a plurality of electrodes 60 disposed on treatment surface 53. Flange 58, contact plate 55, and treatment surface 53 may jointly define treatment chamber 59 (see, e.g., FIG. 10B). Each electrode 40 may be configured to accommodate various geometries of treatment surface 53. In an embodiment, one or more of electrodes 60 may comprise a spiral inductor 62, substantially as described with reference to FIG. 5E. As shown, each spiral inductor/electrode 62/60 may have a substantially arcuate shape or outline. Other shapes and outlines for spiral inductors/electrodes 62/60 are also within the scope of the invention.

In the embodiment of FIG. 5F, treatment chamber 59 may typically have a substantially frusto-conical (truncated cone) shape. However, it is to be understood that the invention is by no means limited to a handpiece having a treatment chamber of a particular shape or geometry.

In an embodiment, handpiece 50 may include a treatment surface 53 configured for contacting an area of the external surface of the skin of at least about 10 cm$^2$, and often treatment surface 53 may be configured for contacting an area of the external surface of the skin of at least about 100 cm$^2$. Handpiece 50 may further include various other elements, features, and characteristics, e.g., as described with reference to FIGS. 1A-B, 3A, and 4.

Figure 6A:
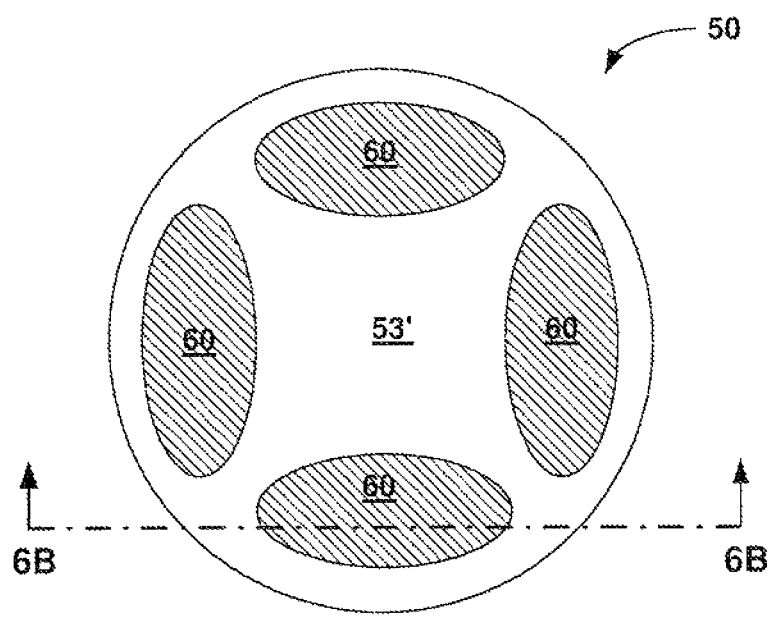
FIG. 6A is a plan view of a treatment surface for a handpiece, according to another embodiment of the invention.

FIG. 6A is a plan view of a treatment surface of a handpiece, according to another embodiment of the invention. Treatment surface 53' may be at least substantially planar. Handpiece 50 may include a plurality of electrodes 60 disposed on treatment surface 53'. Each electrode 60 may be coupled to control unit 30 (see, e.g., FIGS. 1A-B), and an electric potential of each electrode 60 may be independently controlled or adjusted, e.g., relative to a ground pad potential, during a procedure, substantially as described hereinabove (e.g., with reference to FIGS. 1A and 2C). As shown, electrodes 60 may be disposed at least substantially opposite each other on treatment surface 53'. Although electrodes 60 are shown in FIG. 6A as being substantially oval in outline, other configurations for electrodes 60 are also contemplated under the invention. Furthermore, although four (4) electrodes 60 are shown in FIG. 6A, other numbers of electrodes 60 are also within the scope of the invention.

Figure 6B:
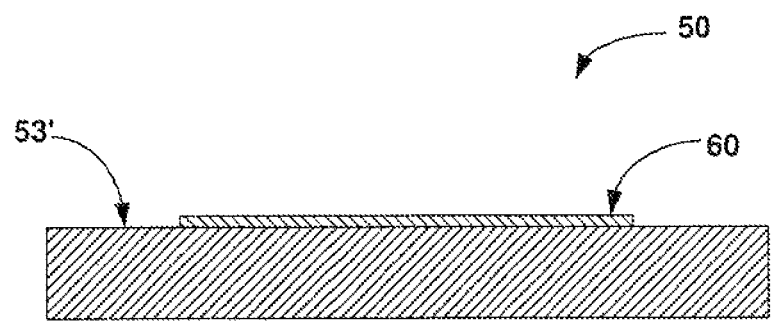
FIG. 6B is a sectional view of the treatment surface as seen along the lines 6B-6B of FIG. 6A.

FIG. 6B is a sectional view of a portion of the handpiece of FIG. 6A, as seen along the lines 6B-6B of FIG. 6A. As can be seen from FIG. 6B, each of electrodes 60 may be at least substantially planar. In an embodiment, each of electrodes 60 may comprise a spiral inductor (see, e.g., FIGS. 7 and 8A-B). During use of handpiece 50, treatment surface 53' may be disposed against a planar or non-planar target region of the patient's skin (not shown in FIG. 6B). In an embodiment, handpiece 50 may be forced against a non-planar target region of the patient's skin such that the skin and adjacent subcutaneous fat may at least substantially conform to treatment surface 53'.

Figure 7:
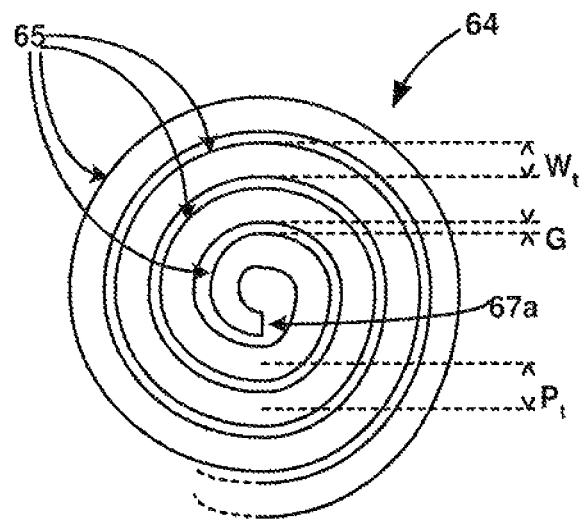
FIG. 7 schematically represents a spiral of electrically conductive material for forming an electrode, as seen in plan view, according to another embodiment of the invention.

FIG. 7 schematically represents a spiral of electrically conductive material, as seen in plan view, according to another embodiment of the invention. Spiral 64 may include a plurality of turns 65 and an inner terminus 67a. In an embodiment, each electrode 60 of handpiece 50 (see, e.g., FIGS. 5D-F and 6A-B) may comprise a spiral 64. In an embodiment, ground pad 40 of system 10 may similarly comprise a spiral 64. Although spiral 64 of FIG. 7 is shown as substantially round, other configurations are also within the scope of the invention. Spiral 64 may comprise a spiral trace of an electrically conductive metal, such as Cu, Al, or various alloys, as non-limiting examples. In an embodiment, spiral 64 may comprise a filament of the electrically conductive metal, wherein the filament may be disposed on a support layer 68 (see, e.g., FIGS. 8A-9B). Only a few of the radially inner turns of spiral 64 are shown in FIG. 7, whereas spiral 64 in its entirety may comprise from about 10 to 200 or more turns, typically from about 10 to 150 turns, and often from about 15 to 100 turns.

As shown in FIG. 7, spiral 64 may have a pitch, $P_t$, representing a radial distance between the radial midpoints of adjacent turns 65. The pitch of spiral 64 may be in the range of from about 0.1 nm i to 10 mm or more, typically from about 0.2 mm to 9 mm, often from about 0.25 to 5 mm, and in some embodiments from about 0.3 mm to 1.5 mm. In an embodiment, the pitch of spiral 64 may be constant or substantially constant. In other embodiments, the pitch of spiral 64 may vary.

Turns 65 of spiral 64 may have a width, $W_t$, wherein the width, $W_t$, is a radial distance across each turn 65. The width of each of turns 65 may typically be in the range of from about 0.05 mm to 10 mm or more, typically from about 0.15 to 9 mm, often from about 0.2 to 5 mm, and in some embodiments from about 0.25 mm to 1.5 mm. In an embodiment, the width of the various turns 65 may be constant or substantially constant. In other embodiments, the width of turns 65 may vary. A profile or cross-sectional shape of turns 65 may be substantially rectangular or rounded; typically the width of each turn 65 may be greater than its height.

A gap, G may exist between adjacent turns 65 of spiral 64, wherein the gap may represent a radial distance between opposing edges of adjacent turns 65. The gap is typically less than the pitch, usually the gap is substantially less than the pitch, and often the gap is considerably less than the pitch. The gap between turns 65 of spiral 64 may typically be in the range of from about 0.1 mm to 0.5 mm, usually from about 0.15 to 0.4 mm, and often from about 0.15 to 0.3 mm. In an embodiment, the gap between adjacent turns 65 may be constant or substantially constant, even though the pitch may be variable. Substantially planar spirals of electrically conductive material suitable for forming spiral inductors are disclosed in commonly assigned, co-pending U.S. patent application Ser. No. 11/966,895, entitled "High Conductivity Inductively Equalized Electrodes and Methods," the disclosure of which is incorporated by reference herein in its entirety.

FIG. 8A schematically represents a spiral inductor, as seen in plan view, according to another embodiment of the invention. Spiral inductor 62 may be used to form an electrode 60 and/or a ground pad 40. Spiral inductor 62 of FIG. 8A may have a substantially circular or oval configuration. Spiral inductor 62 may include a spiral trace 64 of electrically conductive metal including an inner terminus 67a and an outer terminus 67b. In an embodiment, spiral inductor 62 may further include a support layer 68, wherein spiral 64 may be disposed on support layer 68 (see, e.g. FIGS. 9A-B). In an embodiment, support layer 68 may comprise an electrically insulating or dielectric material.

Spiral inductor 62 may include a plurality of turns, from a first turn 65a (radially innermost) to an $n^{th}$ turn 65n (radially outermost). In an embodiment, n may be from about 10 to 200 or more, substantially as described hereinabove. Spiral inductor 62 may have a perimeter, $P_s$, and an external surface area $A_s$ defined by the perimeter. The electrically conductive metal of spiral 64 may occupy at least about 50% of a total surface area $A_s$, that is to say, at least about 50 percent (%) of the external surface area of spiral inductor 62 may be occupied by spiral 64. Typically, electrically conductive metal of spiral 64 may occupy from about 60 to 99% of external surface area, $A_s$; usually from about 70 to 99% of external surface area, $A_s$; often from about 75 to 98% of external surface area $A_s$; and in some embodiments electrically conductive metal of spiral 64 may occupy from about 85% to 97% of external surface area, $A_s$.

FIG. 8B schematically represents a spiral inductor, as seen in plan view, according to another embodiment of the invention. Spiral inductor 62 may be used to form a ground pad 40 and/or an electrode 60 for handpiece 50 according to the instant invention. Spiral inductor 62 may include a spiral trace 64 of electrically conductive metal having an inner terminus 67a, an outer terminus 67b, and a plurality of turns, 65a-n, substantially as described for the embodiment of FIG. 8A. Spiral inductor 62 of FIG. 8B may have a substantially square or rectangular configuration, a perimeter, $P_s$, and a surface area $A_s$ defined by the perimeter. Spiral inductor 62 may include a spiral trace 64 of electrically conductive metal.

Spiral trace 64 may occupy a percentage of surface area, $A_s$, generally as described with reference to FIG. 8A.

It is to be understood that spiral inductor 62 is not limited to a substantially round or rectangular configuration; instead other shapes for spiral inductor 62 are also contemplated under the invention (see, e.g., FIGS. 5E-F). As a non-limiting example, each spiral inductor 62 may have a substantially trapezoidal shape, e.g., comprising a quadrilateral outline having two parallel sides and two non-parallel sides (see, e.g., FIG. 5E). A spiral electrode having such a quadrilateral outline may also have rounded corners. In another embodiment, each spiral inductor 62 may have a substantially arcuate shape or outline (see, e.g., FIG. 5F).

In an embodiment, spiral inductors 62 of FIGS. 8A-B may comprise a spiral 64 which may be at least substantially planar. In an embodiment, spirals 64 and spiral inductors 62 of FIGS. 8A-B may have a slightly curved or contoured outline (see, e.g., FIG. 9B). In an embodiment, spirals 64 and spiral inductors 62 may be curved or contoured to some extent to accommodate or match a slightly curved or contoured treatment surface 53.

Figure 9A:
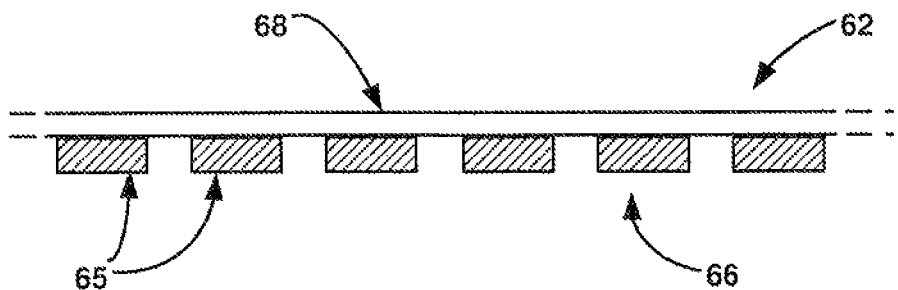
FIG. 9A schematically represents a portion of a spiral inductor for an electrode, as seen in side view, according to an embodiment of the invention.

FIG. 9A schematically represents a portion of a spiral inductor 62 for an electrode 60, as seen in side view, according to an embodiment of the invention. (In comparison with FIGS. 8A-B, which show spiral 64 disposed on top of support layer 68, FIG. 9A shows spiral inductor 62 as being inverted.) As shown in FIG. 9A, spiral inductor 62 may be at least substantially planar.

With further reference to FIG. 9A, spiral inductor 62 may comprise a spiral 64 of electrically conductive metal. In an embodiment, spiral inductor 62 may further comprise a support layer 68, wherein spiral 64 may be disposed on support layer 68. In an embodiment, support layer 68 may be disposed on treatment surface 53 of handpiece 50. In another embodiment, spiral 64 may be disposed directly on treatment surface 53 (i.e., support layer 68 may be omitted). In an embodiment, spiral 64 may be affixed to treatment surface 53 via a layer of electrically insulating adhesive. Stated differently, in an embodiment, support layer 68 may comprise such a layer of electrically insulating adhesive. Spiral 64 may include an external surface 66. External surface 66 may be a bare metal surface of electrically conductive metal spiral 64.

Figure 9B:
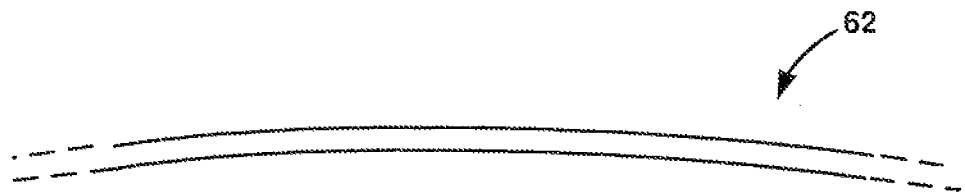
FIG. 9B schematically represents a portion of a spiral inductor for an electrode, as seen in side view, according to another embodiment of the invention.

FIG. 9B schematically represents a portion of a spiral inductor 62 for an electrode 40, as seen in side view, according to another embodiment of the invention. As shown in FIG. 9B, spiral inductor 62 may be at least slightly curved or contoured in outline. Components of spiral inductor 62 in the embodiment of FIG. 9B may be substantially the same as those shown in FIG. 9A and are omitted from FIG. 9B.

In an embodiment, spiral inductor 62 may be configured for direct (e.g., bare metal) contact with the patient. For example, in an embodiment a bare metal external surface 66 of spiral 64 may be configured for contacting the patient. In another embodiment, spiral inductor 62 may include a patient-contacting layer (not shown), comprising electrically conductive or low resistivity material, disposed on spiral 64. A spiral inductor having a patient-contacting layer is disclosed in commonly assigned, co-pending U.S. patent application Ser. No. 11/966,895, entitled "High Conductivity Inductively Equalized Electrodes and Methods," the disclosure of which is incorporated by reference herein in its entirety.

Figure 10A:
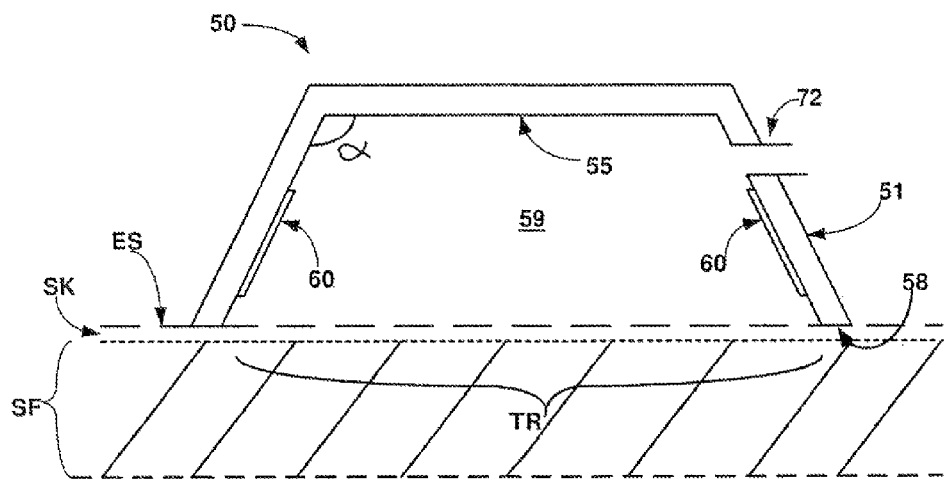
FIG. 10A schematically represents a handpiece, as seen from the side, showing an empty treatment chamber of the handpiece in relation to a target region of skin of a patient, according to one aspect of the invention.

FIG. 10A schematically represents a handpiece, as seen from the side, according to one aspect of the invention. Handpiece 50 may include elements substantially as described hereinabove, including treatment chamber 59 within shell 51, contact plate 55, and a plurality of electrodes 60 disposed on treatment surface 53. In an embodiment, treatment surface 53 may disposed at, or subtend, an angle, $\alpha$, with respect to contact plate 55, wherein angle, $\alpha$ is typically in the range of from about 95 to 175°, usually from about 100 to 165°, and often from about 110 to 160°.

In FIG. 10A, handpiece 50 is disposed against a target region, TR, of the patient's skin, SK, such that flange 58 contacts the external surface, ES, of the skin. In FIG. 10A, suction port(s) 62 may be disconnected from vacuum unit 70 (see, e.g., FIG. 10B), and/or vacuum unit 70 may be idle (off). Accordingly, in FIG. 10A treatment chamber 59 may be seen as empty, e.g., a void that does not contain target tissue of the patient.

Figure 10B:
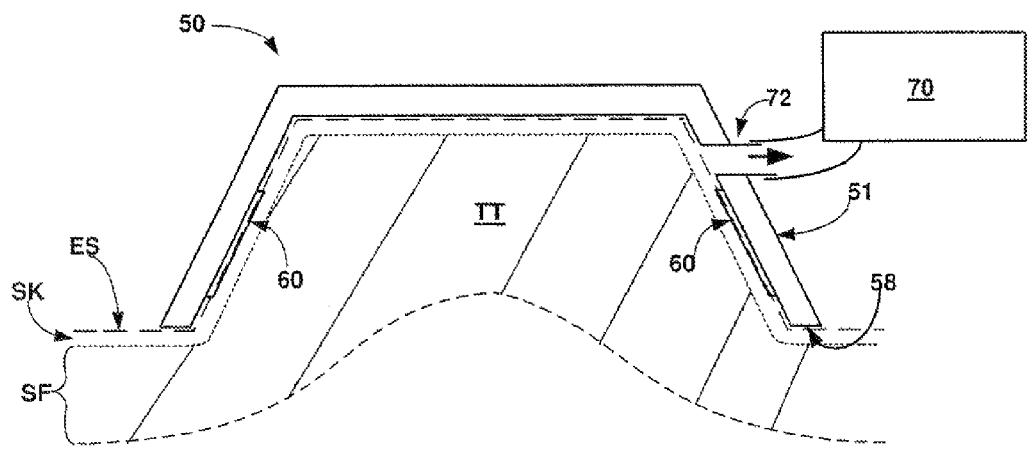
FIG. 10B schematically represents the handpiece of FIG. 10A showing a target tissue of the patient disposed within the treatment chamber, according to another aspect of the invention.

In FIG. 10B, suction port(s) 62 may be connected to vacuum unit 70 and/or vacuum unit 70 may be activated (on). Flange 58 may be adapted for sealing engagement with the external surface of the skin. For example, flange 58 may be configured for sealing treatment chamber 59 against the skin (with or without the application of a sealing material to the skin and/or flange 58). Accordingly, in FIG. 10B target tissue, TT, of the patient may be drawn into treatment chamber 59, such that electrode's 60 and treatment surface 53 may contact the patient's skin, and electrodes 60 may at least partially surround the target tissue (see, e.g., FIGS. 5E-F). Electrodes 60 may be disposed proximal to flange 58, i.e., electrodes 60 may be recessed within treatment chamber 59 such that electrodes 60 do not contact with the patient's tissue/skin unless the target tissue is drawn into treatment chamber 59.

Figure 11A:
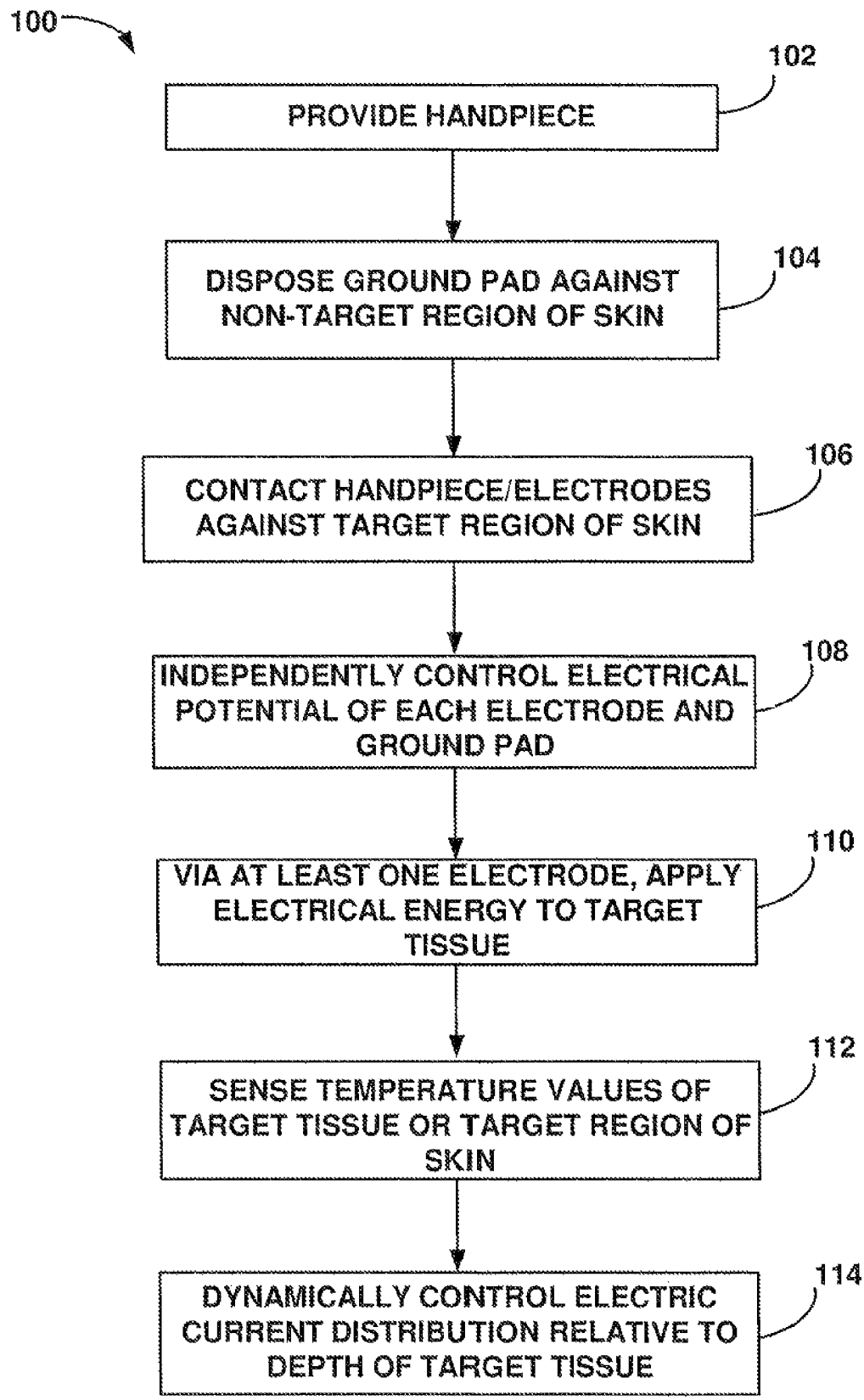
FIG. 11A is a flow chart schematically representing steps in a method for treating a patient, according to another embodiment of the invention.

FIG. 11A is a flow chart schematically representing steps in a method 100 for non-invasively treating a patient, according to another embodiment of the invention. Step 102 may involve providing an electrosurgical handpiece having at least a first electrode and a second electrode (see, e.g., FIGS. 1A-B, 2C, 5D and 6A). At least one of the first and second electrodes may comprise a spiral inductor. At least a portion of the treatment surface may be at least substantially planar. In an embodiment, the treatment surface may occupy at least two different planes. One or more of the spiral inductors may be at least substantially planar, and each spiral inductor may be disposed on a treatment surface of the handpiece. Each spiral inductor may comprise at least one spiral of electrically conductive metal, and each spiral inductor may include various other elements, features, and characteristics as described herein, e.g., with respect to FIGS. 7 and 8A-9B.

Each electrode may be configured for effectively applying electrical energy to the target tissue. The target tissue may be disposed at particular depths beneath a target region of the patient's skin. The target tissue may be disposed within a layer of subcutaneous fat. The target tissue may be disposed at particular depths above a muscle layer of the patient's body. The thickness or depth of the fat layer and of the muscle layer may vary widely from patient to patient and from region to region of the body of a given patient. Each electrode may be configured for effectively applying electrical energy to subcutaneous fat to provide controlled removal, lipolysis, liquefaction, or atrophy of adipose tissue in the targeted region of the patient's body. Advantageously, the instant invention may provide such treatment by selectively heating the targeted subcutaneous fin with little or no heating of adjacent, non-target tissue (skeletal muscle and skin).

Step 104 may involve disposing a ground pad against a non-target region of the patient's skin. The ground pad may comprise a spiral inductor as described hereinabove, e.g., with respect to FIGS. 7 and 8A-9B.

Step 106 may involve contacting the handpiece against the skin of the patient. In an embodiment, step 106 may involve contacting the handpiece against the skin such that at least the first and second electrodes contact a target region of the skin. In an embodiment, the handpiece may have a treatment chamber, and step 106 may involve at least partially drawing the target region of skin and underlying target tissue into the treatment chamber (see, e.g., FIG. 10B). In another embodiment, the handpiece may have a substantially planar treatment surface, and the handpiece may lack a treatment chamber (see, e.g., FIGS. 6A-B).

The target region of the skin and the non-target region of the skin may be non-adjacent to, and remote from, each other. In an embodiment, the target region of the skin and the non-target region of the skin may be separated by at least one layer of subcutaneous fat, at least one layer of muscle, and/or at least one bone of the patient's body. As an example, the target region may be an anterior (ventral) part of the patient's body, while the non-target region may be a posterior (dorsal) part of the patient's body. As further non-limiting examples, the target region may be in the abdominal region or the thoracic region of the patient, while the non-target region may be on the hack or buttocks of the patient (see, e.g., FIG. 12B, infra).

Step 108 may involve independently controlling or adjusting an electric potential of each of: the first electrode, the second electrode, and the ground pad. In an embodiment, step 108 may involve maintaining the ground pad at a reference potential, e.g., ground potential. In an embodiment, step 108 may involve dynamically controlling the electric potential of the first and second electrodes relative to the reference potential. In an embodiment, step 108 may further involve controlling a potential difference between the first electrode and the second electrode. In an embodiment, controlling the potential difference between the first electrode and the second electrode may include controlling or adjusting a phase difference between a first AC voltage of the first electrode and a second AC voltage of the second electrode. The phase difference between the first and second AC voltages may be dynamically controlled or adjusted by increasing or decreasing the phase difference during a procedure. In an embodiment, step 108 may involve independently controlling an electric potential of each of the first electrode, the second electrode, and the ground pad such that each of the first electrode, the second electrode, and the ground pad has a different electric potential.

Step 110 may involve applying electrical energy to the target tissue via at least one of the first and second electrodes. As a non-limiting example, the target tissue may comprise subcutaneous adipose tissue disposed at various depths beneath the target region of the patient's skin.

Step 112 may involve sensing temperature values of the target region of the skin and/or of the target tissue. The temperature values may be sensed by one or more temperature sensors. The temperature sensors may be disposed on the handpiece, e.g., arranged adjacent to one or more of the electrodes. The temperature sensors may be in signal communication with a control unit (see, e.g., FIGS. 1B and 3A).

Step 114 may involve dynamically controlling electric current distribution within the patient's tissues relative to a depth of the target issue such that the target tissue is selectively heated in comparison with adjacent non-target tissue. The target tissue may be disposed at particular depths beneath the target region of the patient's skin. In an embodiment, step 114 may involve controlling the electric current distribution within the patient's tissue in response to temperature values sensed in step 112. The electric current distribution may be sufficient to controllably remove or otherwise modify at least a portion of the target tissue, whereby the appearance of the patient's body or a portion thereof is materially enhanced.

In an embodiment, method 100 may be used to effectively treat an area of the patient's body of at least about 10 cm$^2$, and usually at least about 100 cm$^2$. Naturally, in an embodiment the handpiece may be moved in relation to one or more targeted regions of the patient's body during the procedure in order to treat a relatively large targeted region of the skin of the patient.

Figure 11B:
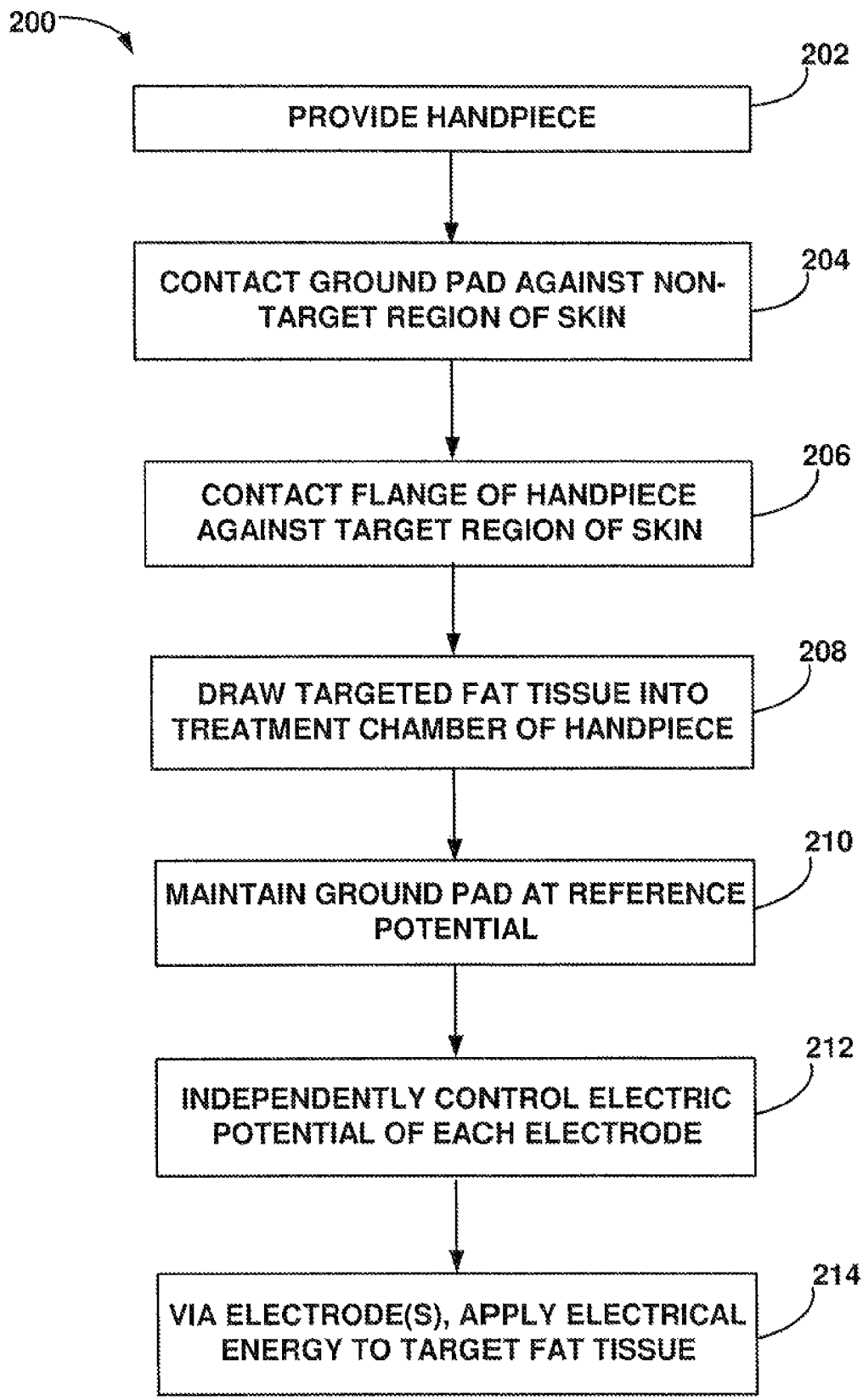
FIG. 11B is a flow chart schematically representing steps in a method for selectively heating a target tissue of a patient, according to another embodiment of the invention.

FIG. 11B is a flow chart schematically representing steps in a method 200 for selectively heating a target tissue of a patient, according to another embodiment of the invention. Step 202 may involve providing a handpiece. The handpiece may include a treatment chamber, a plurality of electrodes disposed within the treatment chamber, and a flange. At least one of the electrodes may comprise a spiral inductor, which may be substantially planar. The treatment chamber may be configured for receiving at least a portion of target tissue therein. A treatment surface of the handpiece may define a portion of the treatment chamber. The electrodes may be disposed on the treatment surface. The flange may define a lower perimeter of the treatment chamber. The handpiece may further include various other elements, features, and characteristics as described herein, e.g., with respect to FIGS. 3A, 4, and 5D-F.

Step 204 may involve contacting a ground pad against a non-target region of the patient's skin. The non-target region may be remote from a target region of the patient's skin, and the target region may be separated from the non-target region by at least one layer of subcutaneous fat, at least one layer of skeletal muscle, and a bone of the patient. The ground pad may comprise a spiral inductor (see, e.g., FIGS. 7 and 8A-B).

Step 206 may involve contacting the flange of the handpiece against a target region of the skin of the patient. In an embodiment, step 204 may involve contacting the patient's skin with the flange such that the flange surrounds the target region of the patient's skin. The target tissue may comprise subcutaneous fat disposed at particular depths beneath the target region of the patient's skin. The depth of the target tissue, as well as the depth of a muscle layer disposed beneath or adjacent to the subcutaneous fat, may vary from patient to patient, as well as from region to region of the body of a single patient.

Step 208 may involve at least partially drawing the target tissue into the treatment chamber of the handpiece. In an embodiment, the target tissue may be drawn into the treatment chamber via suction applied to the treatment chamber. In an embodiment, step 208 may involve drawing the patient's skin against the treatment surface of the handpiece. Each of the electrodes may be disposed proximal to the distal rim (i.e., flange 58) of the handpiece, wherein the electrodes may be recessed within the treatment chamber such that the patient's tissue/skin does not contact any of the electrodes until the target tissue is drawn into the treatment chamber (see, e.g., FIGS. 10A-B).

Step 210 may involve maintaining the ground pad at a reference potential. The reference potential may correspond to ground (earth) potential. Step 212 may involve independently controlling or adjusting the electric potential of each electrode. The electric potential of each electrode may be controlled relative to the reference potential of the ground pad. In an embodiment, step 212 may involve dynamically controlling a potential difference between at least two of the plurality of electrodes mounted on the handpiece. In an embodiment, step 212 may involve increasing or decreasing a phase difference between a first AC voltage of a first electrode and a second AC voltage of a second electrode. In an embodiment, step 212 may involve independently controlling the electric potential of each electrode in response to sensed temperature values of the target region of the patient (see, e.g., FIGS. 1B, 3A, and step 112 of method 100 (FIG. 11A)).

Step 214 may involve applying electrical energy to the target tissue via at least one of the plurality of electrodes. During step 214, the electric current distribution relative to the target tissue may be dynamically controlled, via step 212, to provide selective heating of the target tissue as compared with non-target tissue, wherein the non-target tissue may be disposed adjacent to the target tissue. The target tissue may comprise subcutaneous fat disposed beneath the target region of the patient's skin. The electrical energy applied in step 214 may be controlled (e.g., via steps 210 and 212) to effectively treat or remove at least a portion of the subcutaneous fat, or to improve the appearance of the skin adjacent to the targeted subcutaneous fat.

FIG. 12A schematically represents a portion of a patient's body disposed in relation to a handpiece and a ground pad, according to another embodiment of the invention. A portion of the patient's body, including a target region, TR, of the skin, SK; at least one layer of subcutaneous fat, SF; at least one layer of skeletal muscle, MU; and at least one bone, BN, of the patient, disposed (or "sandwiched") between handpiece 50 and ground pad 40. Handpiece 50 may be disposed against the target region of the skin, while the ground pad 40 may be disposed against a non-target region. NTR, of the skin. Handpiece 50 may be disposed adjacent to a target tissue, TT, beneath the skin, while the ground pad 40 may be disposed at a location remote from the target tissue. The invention is not limited to procedures performed on any particular sequence or orientation of tissue layers.

Figure 12B:
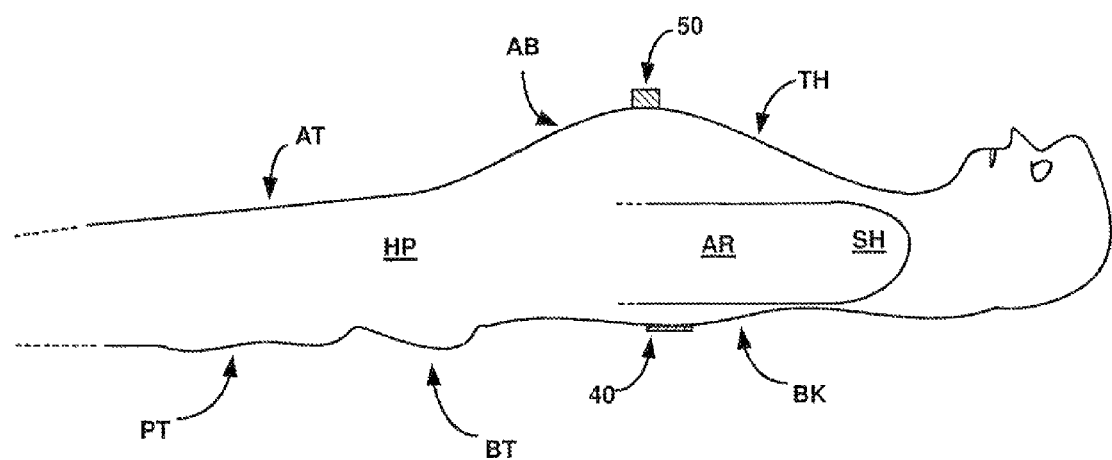
FIG. 12B schematically represents a patient's body, as seen in the medial direction, showing various regions of the body which may comprise target and non-target regions of the patient, according to another embodiment of the invention.

FIG. 12B schematically represents a patient's body, as seen in the medial direction, including various regions of the body which may comprise target or non-target regions of the patient, according to another embodiment of the invention. As non-limiting examples, a target region of the patient on or against which handpiece 50 may be disposed during a procedure for the treatment of cellulite or subcutaneous fat may include the anterior of the thigh, AT, the posterior of the thigh, PT, the buttocks, BT, the back, BK, the abdomen, AB, the arm, AR, the shoulder, SH, the hip, HP, and the thorax, TH. Similarly, a non-target region of the patient on or against which ground pad 40 may be disposed during a procedure for the treatment of cellulite or subcutaneous fat may include, without limitation, the anterior of the thigh, AT, the posterior of the thigh, PT, the buttocks, BT, the hip, HP, the hack, BK, the abdomen, AB, and the thorax, TH. (In FIG. 12B, handpiece 50 and ground pad 40 are shown, for illustrative purposes, against the abdomen and the back, respectively.) A target region of the skin may be disposed above or adjacent to a layer of skeletal muscle, wherein the skeletal muscle may include, without limitation, a thigh muscle, an abdominal muscle, a thoracic muscle, an arm muscle, a shoulder muscle, or a back muscle, or combinations thereof. A target tissue of the patient targeted for treatment according to the invention may comprise subcutaneous adipose tissue disposed between such skeletal muscle layers and the target region(s) of skin. It is to understood, however, that the invention is by no means limited to target tissues in or at the body regions specifically labeled or shown in FIG. 12B. Non-limiting examples of skeletal muscles adjacent to which subcutaneous adipose tissue may be targeted according to the instant invention include: the external oblique muscle, the pectoralis major muscle, the gluteus maximus muscle, the deltoid muscle, the trapezius muscle, the biceps brachii muscle, the triceps brachii muscle, the latissimus dorsi muscle, the rectus femoris muscle, the biceps femoris muscle, the vastus lateralis muscle, and the vastus medialis muscle.

It is to be understood that the foregoing relates to exemplary embodiments of the invention, and that methods and apparatus of the invention may find many applications other than those specifically described herein. Those skilled in the art may devise various mechanisms for controlling electric current distribution relative to particular depths of target tissue beneath the skin, according to the instant invention, in light of applicant's teachings herein. None of the examples presented herein are to be construed as limiting the present invention in any way; modifications may be made without departing from the spirit and scope of the invention as set forth in the following claims.

What is claimed is:

1. A method for treating a patient, comprising:
   a) providing a handpiece having a first electrode and at least one temperature sensor configured for sensing temperature values of a patient's skin;
   b) disposing a ground pad against a non-target region of the patient's skin;
   c) contacting said handpiece against a target region of the patient's skin, such that said first electrode contacts the patient's skin;
   d) determining a temperature value of a target tissue disposed beneath the skin based on the sensed temperature values of the skin; and
   e) controlling an electric potential of said first electrode in response to said determined temperature value of the target tissue for dynamically controlling electric current distribution relative to a depth of the target tissue beneath the skin.

2. The method of claim 1, wherein the non-target region of the skin is remote from the target region of the skin.

3. The method of claim 1, wherein the target region of the skin and the non-target region of the skin are separated by at least one layer of subcutaneous fat, at least one layer of skeletal muscle, or at least one bone of the patient's body.

4. The method of claim 1, wherein the target region of the skin comprises the skin on the abdominal region or the thoracic region of the patient, and the non-target region comprises the skin on the back or buttocks of the patient.

5. The method of claim 1, wherein the target region of the skin is disposed above or adjacent to a layer of skeletal muscle, and wherein the skeletal muscle is selected from a thigh muscle, an abdominal muscle, a thoracic muscle, an arm muscle, a shoulder muscle, and a back muscle, or combinations thereof.

6. The method of claim 5, wherein the skeletal muscle is selected from the external oblique muscle, the pectoralis major muscle, the gluteus maximus muscle, the deltoid muscle, the trapezius muscle, the biceps brachii muscle, the triceps brachii muscle, the latissimus dorsi muscle, the rectus femoris muscle, the biceps femoris muscle, the vastus lateralis muscle, and the vastus medialis muscle, or combinations thereof.

7. The method of claim 5, wherein the target tissue beneath the skin comprises subcutaneous adipose tissue disposed between the skeletal muscle and the target region of the patient's skin.

8. The method of claim 1, wherein step e) comprises: maintaining said ground pad at a reference potential, and controlling said electric potential of said first electrode relative to said reference potential.

9. The method of claim 1, wherein the handpiece comprises a second electrode, and wherein step e) further comprises: controlling a potential difference between said first electrode and said second electrode relative to said ground pad.

10. The method of claim 9, wherein, during step e), each of said first electrode, said second electrode, and said ground pad has a different electric potential.

11. The method of claim 9, wherein step e) comprises controlling a phase difference between a first AC voltage of said first electrode and a second AC voltage of said second electrode.

12. The method of claim 1, wherein said electric current distribution is sufficient to controllably remove or otherwise modify at least a portion of the target tissue beneath the skin.

13. A method for treating a patient, comprising:
  a) contacting a first electrode and a second electrode against a target region of a patient's skin;
  b) disposing a ground pad against a non-target region of the patient's skin;
  c) sensing temperature values of the skin using at least one temperature sensor;
  d) determining a temperature value of a target tissue disposed beneath the skin based on the sensed temperature values of the skin; and
  e) controlling the electric potentials of the first and second electrodes in response to said determined temperature value of the target tissue for selectively heating the target tissue relative to non-target tissue.

14. The method of claim 13, wherein controlling the electric potentials comprises adjusting a phase difference between the electric potentials of the first and second electrodes in response to said determined temperature value of the target tissue.

15. The method of claim 14, wherein controlling the electric potentials the phase difference between the electric potentials of the first and second electrodes is zero.

16. The method of claim 13, wherein controlling the electric potentials of the first and second electrodes comprises dynamically controlling a potential difference between the first and second electrodes.

17. The method of claim 13, wherein the non-target region is disposed at a location remote from the target region of the skin.

18. The method of claim 13, wherein the target tissue comprises subcutaneous adipose tissue disposed between the patient's skin and a skeletal muscle layer.

19. The method of claim 18, wherein the skeletal muscle layer comprises at least one skeletal muscle selected from the external oblique muscle, the pectoralis major muscle, the gluteus maximus muscle, the deltoid muscle, the trapezius muscle, the biceps brachii muscle, the triceps brachii muscle, the latissimus dorsi muscle, the rectus femoris muscle, the biceps femoris muscle, the vastus lateralis muscle, and the vastus medialis muscle.

20. The method of claim 18, wherein the target region of the skin is disposed above or adjacent to a layer of skeletal muscle, and wherein the skeletal muscle is selected from a thigh muscle, an abdominal muscle, a thoracic muscle, an arm muscle, a shoulder muscle, and a back muscle, or combinations thereof.

* * * * *